US011806713B2

(12) United States Patent
Hodko et al.

(10) Patent No.: US 11,806,713 B2
(45) Date of Patent: Nov. 7, 2023

(54) MICROFLUIDIC SYSTEM BASED ON ACTIVE CONTROL OF FLOW RESISTANCE IN MICROFLUIDIC CHANNELS AND METHODS OF USE THEREOF

(71) Applicant: Nexogen, Inc., San Diego, CA (US)

(72) Inventors: Dalibor Hodko, Poway, CA (US); Nives Hodko, Poway, CA (US); Anne-Laure Petit, San Diego, CA (US); Ulrich Niemann, Seattle, WA (US)

( * ) Notice: Subject to any disclaimer, the term of this patent is extended or adjusted under 35 U.S.C. 154(b) by 94 days.

(21) Appl. No.: 17/537,439

(22) Filed: Nov. 29, 2021

(65) Prior Publication Data
US 2022/0168738 A1   Jun. 2, 2022

Related U.S. Application Data

(60) Provisional application No. 63/119,421, filed on Nov. 30, 2020, provisional application No. 63/119,362, filed on Nov. 30, 2020.

(51) Int. Cl.
| | |
|---|---|
| C12N 15/10 | (2006.01) |
| B01L 3/00 | (2006.01) |
| G01N 35/10 | (2006.01) |
| B01L 3/02 | (2006.01) |
| B29C 65/16 | (2006.01) |
| G01N 35/00 | (2006.01) |

(52) U.S. Cl.
CPC ..... *B01L 3/502746* (2013.01); *B01L 3/50273* (2013.01); *G01N 35/00069* (2013.01); *B01L 2200/16* (2013.01); *B01L 2300/0645* (2013.01); *B01L 2300/0819* (2013.01); *B01L 2400/0415* (2013.01); *B01L 2400/0463* (2013.01); *B01L 2400/0487* (2013.01); *B01L 2400/082* (2013.01)

(58) Field of Classification Search
CPC ........... B01L 3/502746; B01L 3/50273; B01L 2200/16; B01L 2300/0645; B01L 2300/0819; B01L 2400/0415; B01L 2400/0463; B01L 2400/0487; B01L 2400/082; G01N 35/00069
See application file for complete search history.

(56) References Cited

U.S. PATENT DOCUMENTS

2022/0032294 A1\*   2/2022   Escajeda ................... B01L 7/52

\* cited by examiner

*Primary Examiner* — Jennifer Wecker
*Assistant Examiner* — Oyeleye Alexander Alabi
(74) *Attorney, Agent, or Firm* — Edward Ergenzinger

(57) ABSTRACT

The invention relates to a microfluidic system based on active control of flow resistance and balancing pressures in microfluidic channels and an improved method for disposable microfluidic devices and cartridges for use in, but not limited to, in-vitro diagnostics. The microfluidic system and device of the invention does not utilize mechanical moving parts to control the fluid flow and has no external fluidic connection to the instrument or fluidics controller.

32 Claims, 13 Drawing Sheets

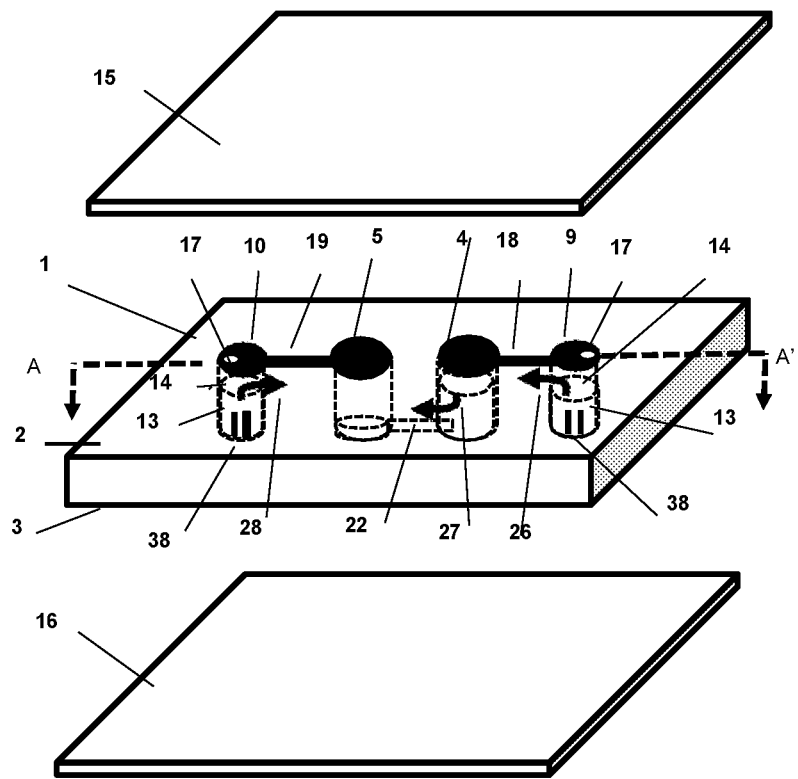
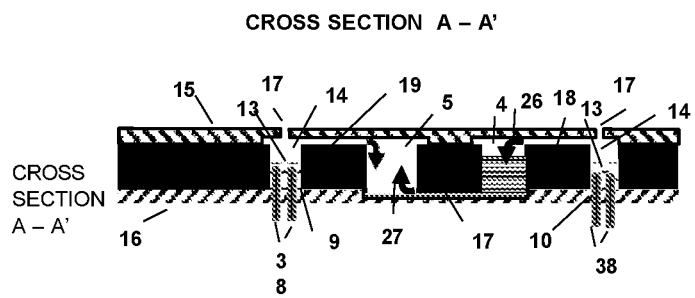
FIG. 1

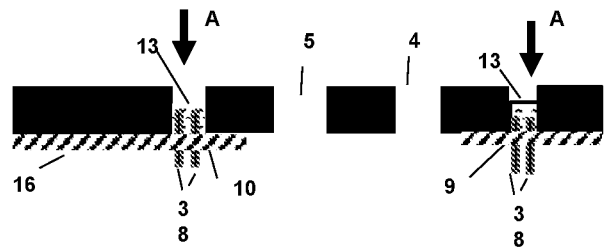
Fig. 2 a
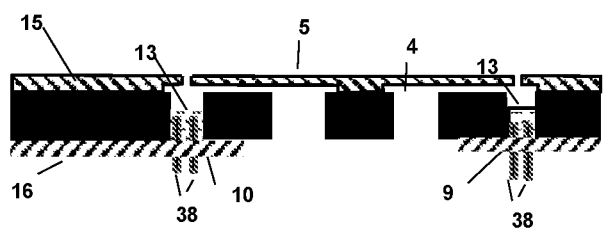
Fig. 2 b
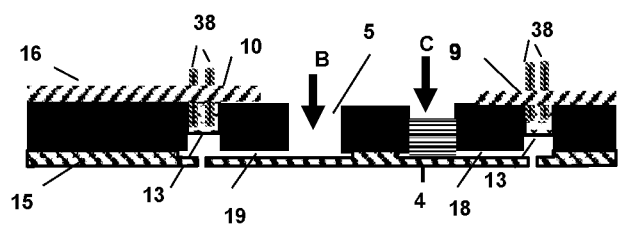
Fig. 2 c
FIGS. 2A-2C

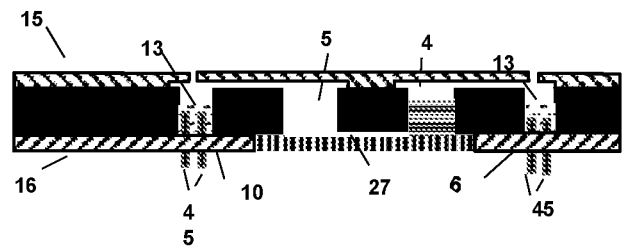
Fig. 2 d
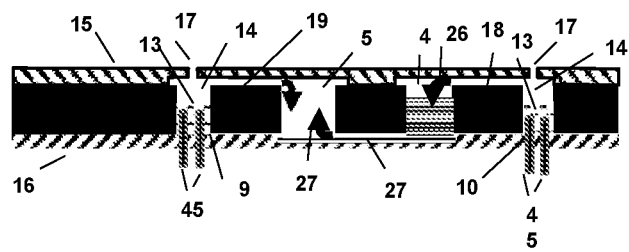
Fig. 2 e
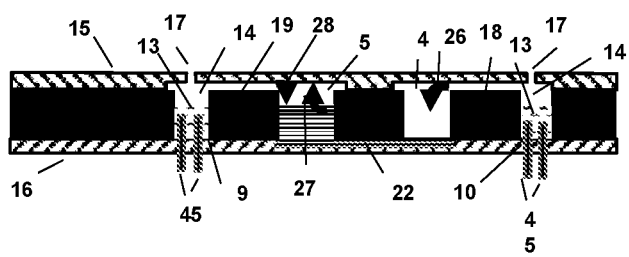
Fig. 2 f
FIGS. 2D-2F

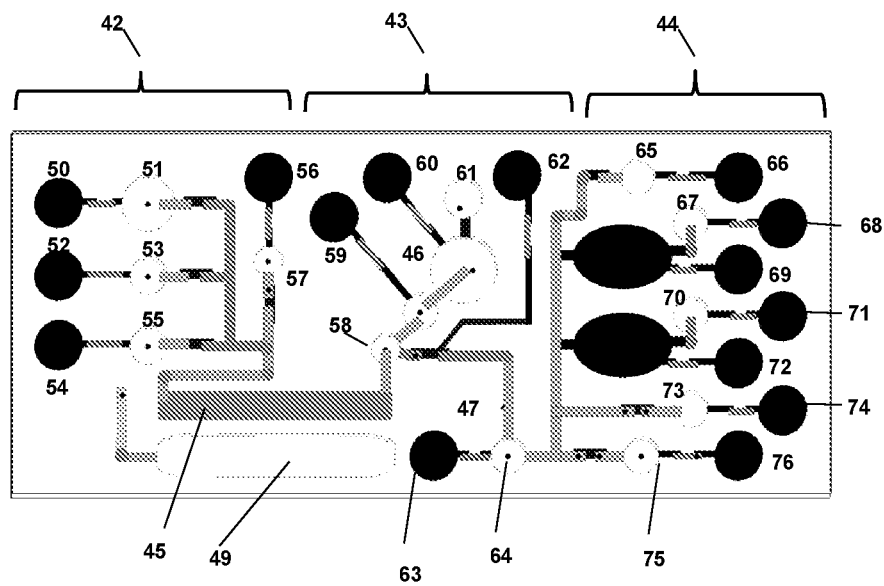
Fig. 5 a
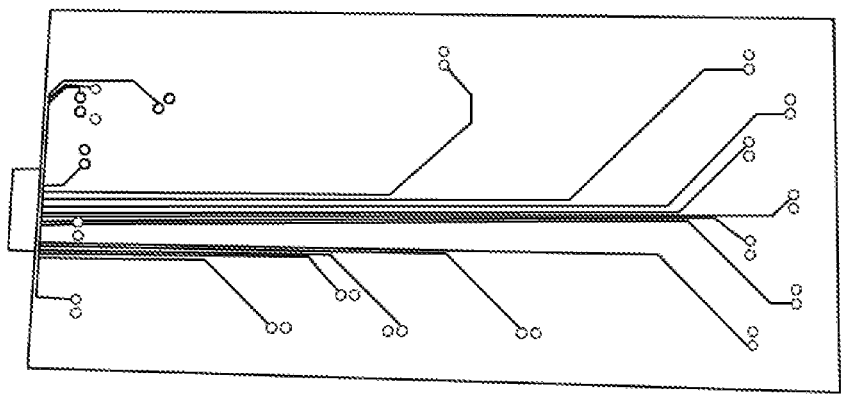
Fig. 5b
FIG. 5

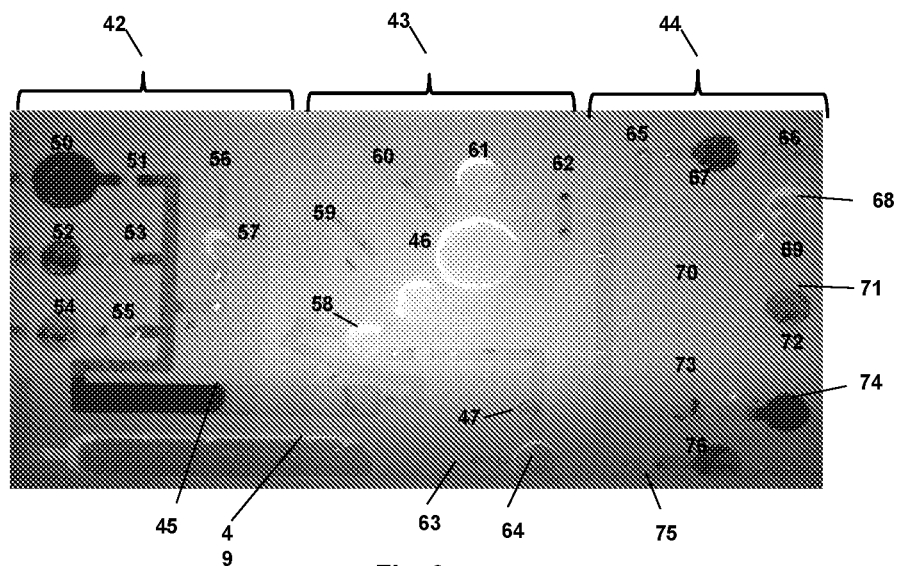
Fig. 6a
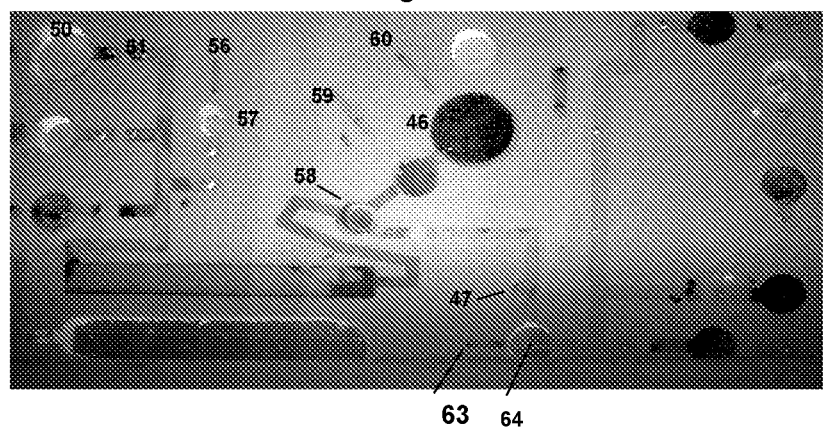
Fig. 6b
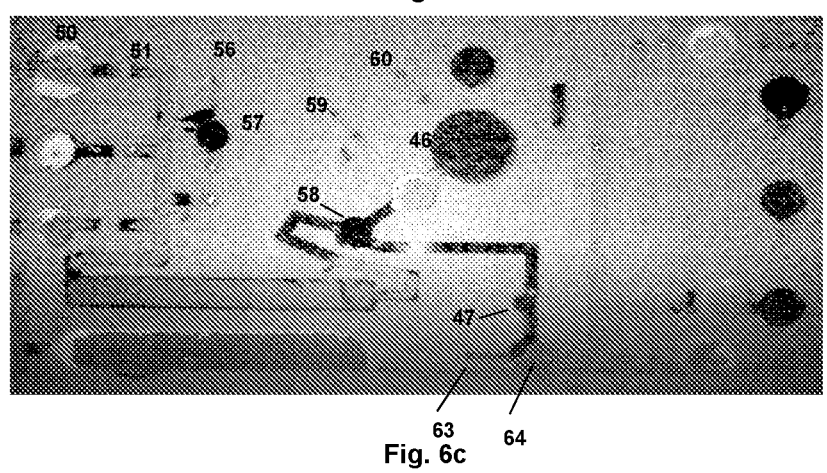
Fig. 6c
FIG. 6

| | Current | Entire Reagent to Magnetic Chamber (sec) | Magnetic Chamber (sec) | Reagent to Waste (sec) | Reagent to Array (sec) | SAMPLE PREP Total Time (minutes) |
|---|---|---|---|---|---|---|
| Sample (1 mL) | 90 mA | 85 | 113 | 142 | | |
| Wash 1 (400 µl) | 90 mA | 25 | 53 | 88 | | 6:54 min |
| Wash 2 (400 µl) | 90 mA | 25 | 49 | 73 | | |
| Eluent (200 µl) | 90 mA | 11 | 43 | | 59 | |
| Sample (1 mL) | 200 mA | 47 | 67 | 78 | | |
| Wash 1 (400 µl) | 200 mA | 15 | 29 | 42 | | 4:34 min |
| Wash 2 (400 µl) | 200 mA | 16 | 30 | 40 | | |
| Eluent (200 µl) | 200 mA | 13 | 27 | | 35 | |
| Sample (1 mL) | 300 mA | 28 | 33 | 38 | | |
| Wash 1 (400 µl) | 300 mA | 10 | 15 | 23 | | 2:33 min |
| Wash 2 (400 µl) | 300 mA | 12 | 14 | 22 | | |
| Eluent (200 µl) | 300 mA | 7 | 15 | | 22 | |

| START | CONTINUATION |
|---|---|
| | Wait,38 |
| 1-sample; | PumpCurrent,1,0 |
| 2 wash1; | PumpCurrent,2,0 |
| 3 wash2; | PumpCurrent,3,0 |
| 6 eluent; | PumpCurrent,4,0 |
| 4,5 resistance control pumps; | PumpCurrent,5,0 |
| | Wait,5 |
| PumpCurrent,1,0.09 | PumpCurrent,6,0.09 |
| Wait,35 | PumpCurrent,1,0.01 |
| PumpCurrent,4,.09 | PumpCurrent,2,0.01 |
| PumpCurrent,5,.08 | Wait,10 |
| Wait,85 | PumpCurrent,8,0.06 |
| PumpCurrent,1,0.01 | PumpCurrent,1,0 |
| PumpCurrent,4,0 | PumpCurrent,2,0 |
| PumpCurrent,5,0 | Wait,20 |
| Wait,1 | PumpCurrent,7,0.09 |
| PumpCurrent,2,0.09 | Wait,15 |
| Wait,30 | PumpCurrent,7,0 |
| PumpCurrent,4,.09 | PumpCurrent,8,0 |
| PumpCurrent,5,.08 | PumpCurrent,6,0 |
| Wait,35 | Wait,45 |
| PumpCurrent,2,0 | |
| PumpCurrent,4,0 | |
| PumpCurrent,5,0 | |
| PumpCurrent,1,0 | |
| Wait,1 | |
| PumpCurrent,3,0.09 | |
| PumpCurrent,1,0.01 | |
| PumpCurrent,2,0.01 | |
| Wait,28 | |
| PumpCurrent,4,0.09 | |
| PumpCurrent,5,0.08 | |

FIG. 9

MICROFLUIDIC SYSTEM BASED ON ACTIVE CONTROL OF FLOW RESISTANCE IN MICROFLUIDIC CHANNELS AND METHODS OF USE THEREOF

CROSS-REFERENCE TO RELATED APPLICATIONS

The present invention is a U.S. Utility patent application that claims priority to U.S. Provisional Patent Application No. 63/119,362, filed on Nov. 30, 2020, and U.S. Provisional Patent Application No. 63/119,421, filed on Nov. 30, 2020, the entire disclosures of which are incorporated herein by reference.

GOVERNMENT INTEREST

This invention was made with government support under 5 R44 HD084019-03 awarded by the National Institutes of Health. The United States Government has certain rights in the invention.

FIELD OF THE INVENTION

The present invention relates to microfluidics and microfluidics devices and disposable cartridges generally used in in-vitro diagnostics.

BACKGROUND OF THE INVENTION

Various apparatuses and methods for controlling the flow in microfluidics devices are known in the art. The control of the fluid or liquid flows in the microfluidics devices generally is determined by the flow resistance elements in the channels that is determined by their design based on their geometrical shape or surface properties of the materials used presenting passive resistance elements embedded into the design that are not changed in the operation of the device. Active control of the fluid movement direction is often based on mechanical barriers and mechanical moving parts that are pushed, pulled, inserted within the channels to control the flow, typically representing different mechanisms of valves that regulate the flow in the channels. The fluid is pumped mostly using external devices such as syringes or push pins operated from an instrument, e.g., a robotized system that regulate the flow rate. The push pins are used in pouch type fluidics (where the reagents are stored in flexible pouches and pushed into the microfluidic channels by squeezing the pouches using push pins and an external system to actuate the pins (U.S. Pat. No. 89,405,226 B2, Self-contained Biological Analysis). The systems utilizing soft materials, such as polydimethyl siloxane (PDMS) are often used where multilayer PDMS channels are created as a part of a microfluidic device (U.S. Pat. No. 9,952,126 B2, Methods of Multiple Single-Cell Capturing and Processing Using Microfluidics; U.S. Pat. No. 8,129,176 B2, Integrated Active Flux Microfluidic Devices and Methods), one layer serving to push air from an external source, and enclose the underlying channels by bending the PDMS material, acting as valves in the underlying PDMS channels. On-chip pumping systems have been designed using complex manufacturing processes including silicon micromachining, where, e.g., the miniature valves or pumps are made using thin silicon-based diaphragm that change shape under applying voltages over the diaphragms. However, silicon-based valves/pumps for microfluidic systems (U.S. Pat. No. 8,690,830 B2, In-Plane Electromagnetic MEMS Pumps; US 20090314368 A1, Microfluidics System Comprising Pinch Valve and On-Chip MEMS Pump) as well as polymer-based MEMS for microfluidics (U.S. Pat. No. 6,136,212 A, Polymer-based Micromachining for Microfluidics Devices) did not find broad applications in disposable devices, such as cartridges in in-vitro diagnostics systems because of their high cost of manufacturing and low fluid volumes that are often not compatible with larger, mL volume clinical samples. The flow resistance in the microfluidic channels can be determined during the design of the devices using their geometry, i.e., width, length, meandering, narrowing, widening of the channels or pre-designing the so-called burst pressures when the fluid from one chamber enters the channel. The burst pressures, i.e., the pressure needed to overcome the resistance for the fluid to continue flowing is determined by surface properties of the material and shape of the fluidic channels. Thus, the materials, or even coatings with different hydrophobicity or hydrophilicity can be used to modify the resistance to flow in the fluidic channels. However, these passive flow resistance properties are frozen into the design of the fluidics device during the fabrication or filling process of the device, and cannot be changed during the use of the device, unless a movement of mechanical additional elements is used externally or internally to operate the device.

SUMMARY OF THE INVENTION

To address the foregoing problems, in whole or in part, and/or other problems that may have been observed by persons skilled in the art, the present disclosure provides compositions and methods as described by way of example as set forth below.

A microfluidic system based on active control of flow resistance in microfluidic channels is provided, comprising:
  a) a microfluidic device comprising a housing, wherein the housing comprises a top end and a bottom end;
  b) a plurality of reagent chambers and a plurality of pressure-generating chambers, wherein the reagent chambers and the pressure-generating chambers are positioned in the housing, and wherein:
    i) the pressure-generating chambers produce a pressure-generating fluid using no mechanical moving parts;
    ii) the reagent chambers are connected by at least one gas channel at the top end of the housing to at least one of the pressure-generating chambers; and
    iii) the reagent chambers are connected by one or more liquid channels at the bottom end of the housing to one or more of the pressure-generating chambers;
  c) a top substrate enclosing the pressure-generating fluid chambers, wherein the top substrate comprises fluidic channels connecting the pressure-generating chambers to one or more vent holes, thereby enabling movement of one or more reagent fluids in the one or more liquid channels at the bottom end of the housing; and
  d) a bottom substrate enclosing the reagent chambers; wherein the movement of the one or more reagent fluids is enabled by activating the one or more pressure-generating chambers to pump the pressure-generating fluid toward the one or more reagent chambers and controlling and balancing pressure of the pressure-generating fluid to achieve active flow resistance resulting in the movement of the one or more reagent fluids in a desired direction; and wherein the microfluidic system is configured to achieve passive flow resistance during filling of the microfluidic device with the pressure-generating fluid to prevent mixing of the pressure-generating fluid with the reagents when the microfluidic system is not in operation. In some embodiments, achieving passive flow resistance during filling of the microfluidic device comprises the steps of:

aa) filling the plurality of pressure-generating chambers with pressure-generating fluid;

bb) enclosing the housing and the plurality of pressure-generating fluid chambers, the gas channels, and the plurality of reagent chambers with the top substrate such that the fluidic channels make desired connections between the chambers and vent holes enabling movement of one or more reagent fluids in liquid channels at the bottom end of the housing; and cc) inverting the microfluidic device and filling the plurality of reagent chambers with the one or more reagent fluids and enclosing the reagent chambers, the one or more reagent fluids, and the liquid channels with a bottom substrate at the bottom end of the housing.

In some embodiments, the microfluidic system further comprises an automated electronics interface and software control configured to control and balance the pressure of the pressure-generating fluid, wherein the automated electronics interface and software control is programmed to execute a reproducible protocol for operation of the microfluidic device.

In some embodiments, the pressure of the pressure-generating fluid in the plurality of pressure-generating chambers is generated using electrolytic gas evolution.

In some embodiments, the pressure of the pressure-generating fluid in the plurality of pressure-generating chambers is generated using thermal heating, catalytic heating, ultrasonic means, electrophoretic means, or dielectrophoretic means.

In some embodiments, the microfluidic device is configured to control the pressure of the pressure-generating fluid electronically using electrodes, electronic contacts, and/or switches embedded in the housing.

In some embodiments, the one or more reagent fluids comprise one or more reagents for extraction, amplification, or detection of one or more analytes comprising one or more biomarkers, nutrients, and/or chemicals.

In some embodiments, the one or more pressure-generating fluids comprise aqueous or non-aqueous liquids.

In some embodiments, the one or more vent-holes are embedded within the top substrate of the housing atop one or more pressure-generating chambers or one or more reagent chambers.

In some embodiments, the pressure of the pressure-generating fluid ranges from about 0.1 psi to about 1,000 psi, particularly from about 0.1 psi to about 100 psi.

In some embodiments, electrolytic gas evolution generates the pressure of the pressure-generating fluid by electrolysis of the pressure-generating fluid, wherein the pressure-generating fluid comprises water, an inorganic salt solution, or a conductive organic solution, and wherein electrolysis of the pressure-generating fluid produces a gas comprising oxygen, hydrogen, and/or chlorine.

In some embodiments, the microfluidic system further comprises one or more electrodes for electrolytic gas evolution, wherein the one or more electrodes comprise anodic corrosion-stable noble metal electrodes or one or more anodically sacrificial electrodes, wherein the one or more anodically sacrificial electrodes comprise stainless steel, aluminum, copper, carbon, carbon inks, plated electrodes, and/or screen-printed electrodes.

In some embodiments, the microfluidic system is configured to enable the gas produced by electrolysis to control pH and/or conductivity reactions in the one or more of the plurality of reagent chambers.

In some embodiments, the microfluidic system further comprises one or more gas permeable membranes atop the plurality of pressure generation chambers, wherein the one or more gas permeable membranes separate liquid and gas pressure-generating fluids in the pressure-generating chambers while allowing permeation of pressure-generating fluid into the fluidic channels without mixing between the pressure-generating fluid and the one or more reagent fluids in the plurality of reagent chambers.

In some embodiments, the microfluidic system is configured to pump the pressure-generating fluid toward one of the plurality of reagent chambers that comprises one of the vent holes, or wherein the pressure-generating fluid is pumped toward one of the plurality of pressure generation chambers that comprises a vent hole, thereby causing a high flow velocity and generating a Venturi vacuum, wherein the Venturi vacuum enables control of fluid flow resistance and/or fluid flow velocity.

A method is also provided for actively controlling flow resistance in microfluidic channels of a microfluidic system, comprising:

a) providing a microfluidic system comprising a microfluidic device, wherein the microfluidic device comprises:
  i) a housing, wherein the housing comprises a top end and a bottom end;
  ii) a plurality of reagent chambers and a plurality of pressure-generating chambers, wherein the reagent chambers and the pressure-generating chambers are positioned in the housing, and wherein:
    aa) the pressure-generating chambers produce a pressure-generating fluid using no mechanical moving parts;
    bb) the reagent chambers are connected by at least one gas channel at the top end of the housing to at least one of the pressure-generating chambers; and
    cc) the reagent chambers are connected by one or more liquid channels at the bottom end of the housing to one or more of the pressure-generating chambers;
  iii) a top substrate enclosing the pressure-generating fluid chambers, wherein the top substrate comprises fluidic channels connecting the pressure-generating chambers to one or more vent holes, thereby enabling movement of one or more reagent fluids in the one or more liquid channels at the bottom end of the housing; and
  iv) a bottom substrate enclosing the reagent chambers; wherein the microfluidic system is configured to achieve passive flow resistance during filling of the microfluidic device with the pressure-generating fluid to prevent mixing of the pressure-generating fluid with the reagents when the microfluidic system is not in operation; and b) activating the one or more pressure-generating chambers to pump the pressure-generating fluid toward the one or more reagent chambers and controlling and balancing pressure of the pressure-generating fluid to achieve active flow resistance resulting in the movement of the one or more reagent fluids in a desired direction, wherein the movement of the one or more reagent fluids is enabled.

In some embodiments, the method for actively controlling flow resistance in microfluidic channels of a microfluidic system comprises achieving passive flow resistance during filling of the microfluidic device, further comprising the steps of:

ai) filling the plurality of pressure-generating chambers with pressure-generating fluid;

bi) enclosing the housing and the plurality of pressure-generating fluid chambers, the gas channels, and the plurality of reagent chambers with the top substrate such that the fluidic channels make desired connections between the chambers and vent holes enabling movement of one or more reagent fluids in liquid channels at the bottom end of the housing; and ci) inverting the microfluidic device and filling the plurality of reagent chambers with the one or more reagent fluids and enclosing the reagent chambers, the one or more reagent fluids, and the liquid channels with a bottom substrate at the bottom end of the housing.

In some embodiments, the method for actively controlling flow resistance in microfluidic channels of a microfluidic system is executed by an automated electronics interface and software control configured to control and balance the pressure of the pressure-generating fluid, wherein the automated electronics interface and software control is programmed to execute a reproducible protocol for operation of the microfluidic device.

In some embodiments of the method for actively controlling flow resistance in microfluidic channels of a microfluidic system, the pressure of the pressure-generating fluid in the plurality of pressure-generating chambers is generated using electrolytic gas evolution.

In some embodiments of the method for actively controlling flow resistance in microfluidic channels of a microfluidic system, the pressure of the pressure-generating fluid in the plurality of pressure-generating chambers is generated using thermal heating, catalytic heating, ultrasonic means, electrophoretic means, or dielectrophoretic means.

In some embodiments of the method for actively controlling flow resistance in microfluidic channels of a microfluidic system, the microfluidic device is configured to control the pressure of the pressure-generating fluid electronically using electrodes, electronic contacts, and/or switches embedded in the housing.

In some embodiments of the method for actively controlling flow resistance in microfluidic channels of a microfluidic system, the one or more reagent fluids comprise one or more reagents for extraction, amplification, or detection of one or more analytes comprising one or more biomarkers, nutrients, and/or chemicals.

In some embodiments of the method for actively controlling flow resistance in microfluidic channels of a microfluidic system, the one or more pressure-generating fluids comprise aqueous or non-aqueous liquids.

In some embodiments of the method for actively controlling flow resistance in microfluidic channels of a microfluidic system, the one or more vent-holes are embedded within the top substrate of the housing atop one or more pressure-generating chambers or one or more reagent chambers.

In some embodiments of the method for actively controlling flow resistance in microfluidic channels of a microfluidic system, the pressure of the pressure-generating fluid ranges from about 0.1 psi to about 1,000 psi, particularly from about 0.1 psi to about 100 psi.

In some embodiments of the method for actively controlling flow resistance in microfluidic channels of a microfluidic system, electrolytic gas evolution generates the pressure of the pressure-generating fluid by electrolysis of the pressure-generating fluid, wherein the pressure-generating fluid comprises water, an inorganic salt solution, or a conductive organic solution, and wherein electrolysis of the pressure-generating fluid produces a gas comprising oxygen, hydrogen, and/or chlorine.

In some embodiments of the method for actively controlling flow resistance in microfluidic channels of a microfluidic system, the microfluidic system further comprises one or more electrodes for electrolytic gas evolution, wherein the one or more electrodes comprise anodic corrosion-stable noble metal electrodes or one or more anodically sacrificial electrodes, wherein the one or more anodically sacrificial electrodes comprise stainless steel, aluminum, copper, carbon, carbon inks, plated electrodes, and/or screen-printed electrodes.

In some embodiments of the method for actively controlling flow resistance in microfluidic channels of a microfluidic system, the microfluidic system is configured to enable the gas produced by electrolysis to control pH and/or conductivity reactions in the one or more of the plurality of reagent chambers.

In some embodiments of the method for actively controlling flow resistance in microfluidic channels of a microfluidic system, the microfluidic system further comprises one or more gas permeable membranes atop the plurality of pressure generation chambers, wherein the one or more gas permeable membranes separate liquid and gas pressure-generating fluids in the pressure-generating chambers while allowing permeation of pressure-generating fluid into the fluidic channels without mixing between the pressure-generating fluid and the one or more reagent fluids in the plurality of reagent chambers.

In some embodiments of the method for actively controlling flow resistance in microfluidic channels of a microfluidic system, the microfluidic system is configured to pump the pressure-generating fluid toward one of the plurality of reagent chambers that comprises one of the vent holes, or wherein the pressure-generating fluid is pumped toward one of the plurality of pressure generation chambers that comprises a vent hole, thereby causing a high flow velocity and generating a Venturi vacuum, wherein the Venturi vacuum enables control of fluid flow resistance and/or fluid flow velocity.

Additional features of the invention will be or will become apparent to one with skill in the art upon examination of the following figures and detailed description. It is intended that all such additional features and advantages be included within this description, be within the scope of the invention, and be protected by the accompanying claims.

BRIEF DESCRIPTION OF THE DRAWINGS

Figures 3, 3A, 3B:
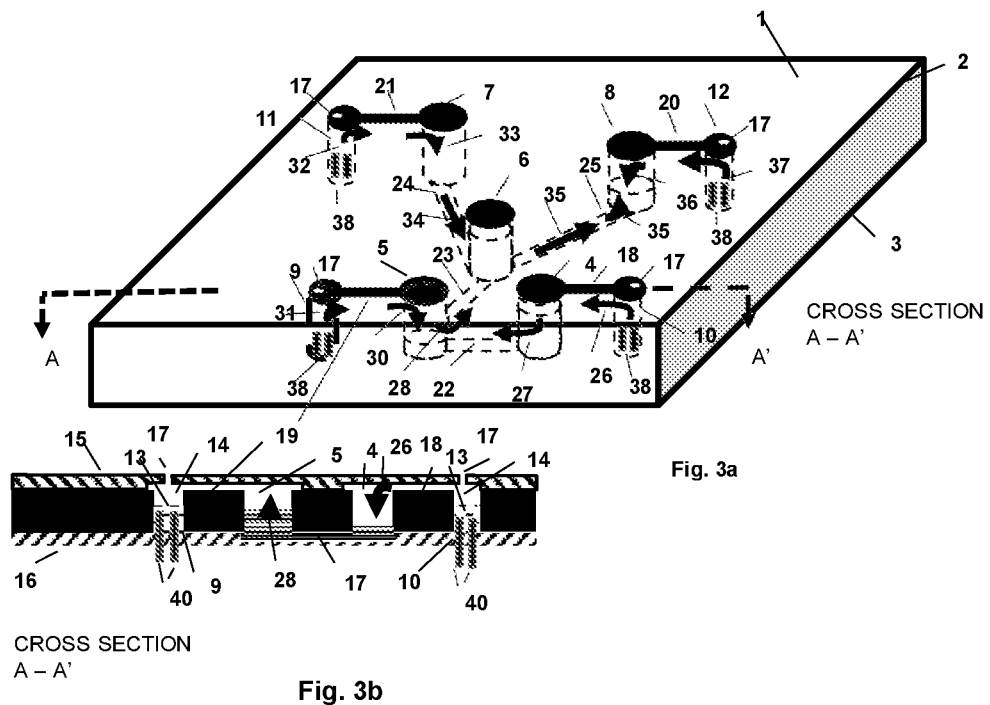
Figure 4A:
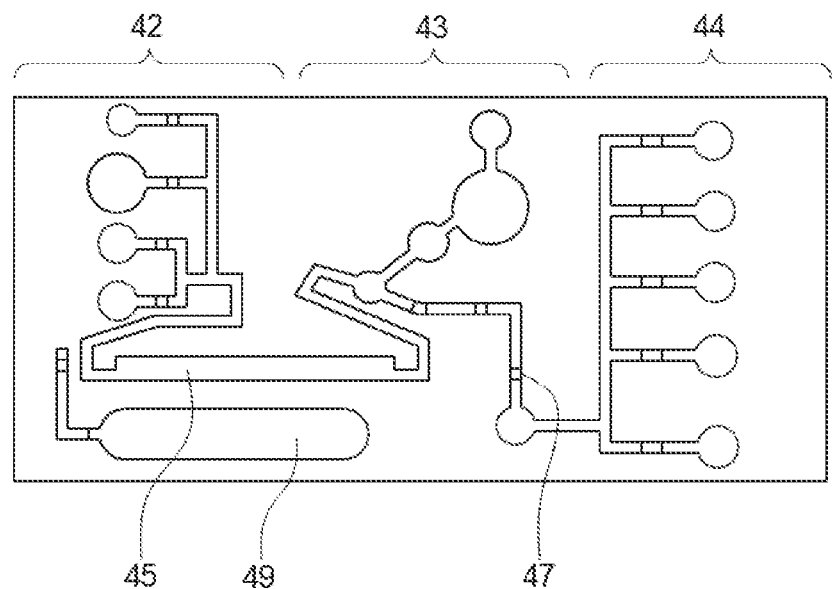
Figure 4C:
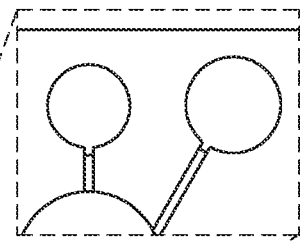
Figure 4B:
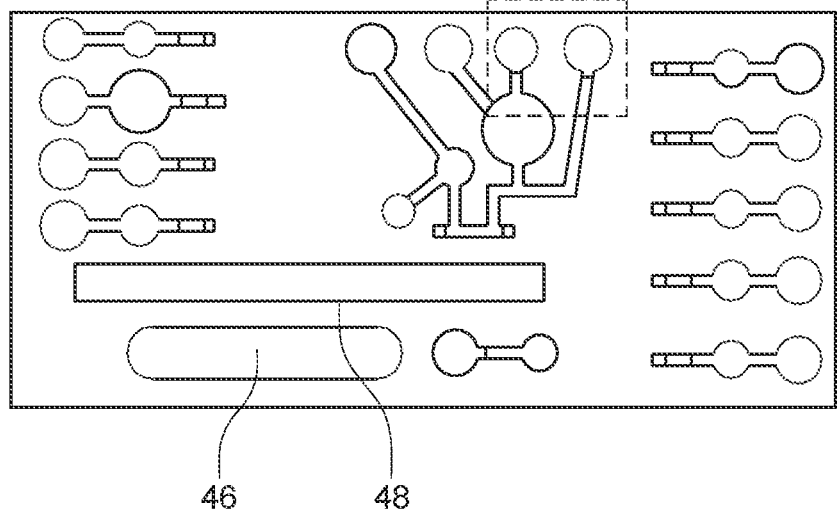

Having thus described the subject matter of the present invention in general terms, reference will now be made to the accompanying drawings, which are not necessarily drawn to scale, and wherein:

FIG. 1A is a simplified exploded view illustration of the microfluidic device constructed and operative in accordance with an embodiment of the present invention and FIG. 1 B is a cross section of the housing of the device where simple back-and-forth pumping is demonstrated between two reagent chambers;

FIGS. 2A, 2B, 2C, and 2D are a cross section of the housing of the microfluidic device showing typical initial steps of assembly of the microfluidic device, order of filling the fluids and achieving a passive resistance in fluid channels that prevents mixing of fluids between pressure-generating chambers and reagent chambers;

FIGS. 2E and 2F are a cross section of the housing of the microfluidic device showing active control of resistance in a fluidic channel and transfer of reagent fluid between the chambers by controlling the pressure in pressure-generating chambers;

FIGS. 3A and 3B are simplified pictorial illustrations of typical further steps in the operation of the microfluidic device of the invention of another embodiment with multiple pressure generation and reagent chambers and controlling a flow through active flow resistance control by balancing pressures in the fluidic channels;

FIGS. 4A, 4B, and 4C are photographs of a manufactured microfluidic device of the invention, 4A showing the top view of the microfluidic device, cartridge, and 4B bottom view of the same cartridge, where 4C present an insert from the photograph in 4B showing a closeup of a electrolytic pump;

FIG. 5A illustrates a pictorial schematic of a manufactured microfluidic device, a cartridge for the performance of in-vitro diagnostic testing for sample-to-answer analysis of DNA, RNA or protein testing on a single cartridge.

Figure 7A:
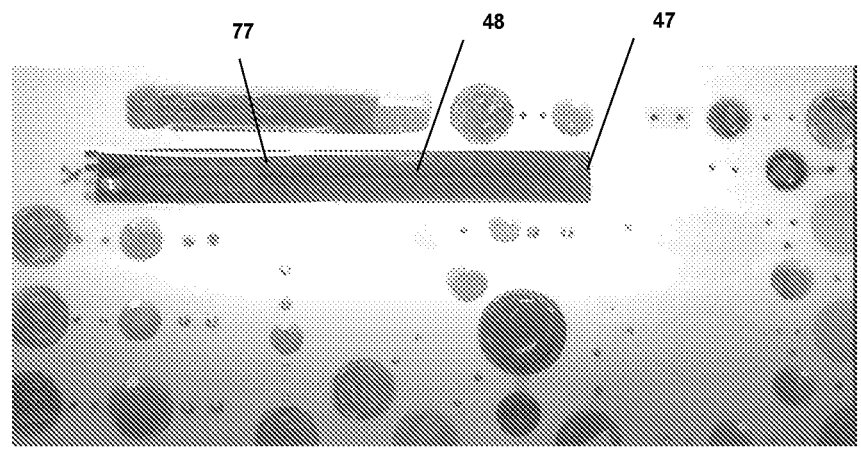
Figure 7B:
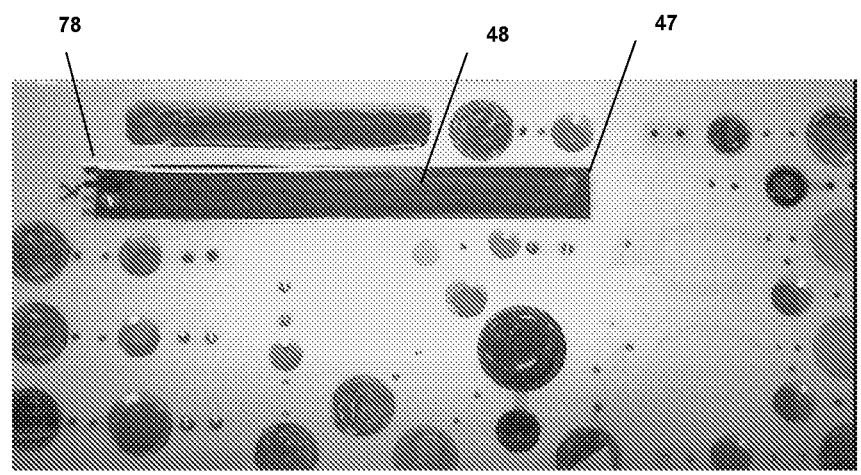
Figures 8A, 8B, 8C:
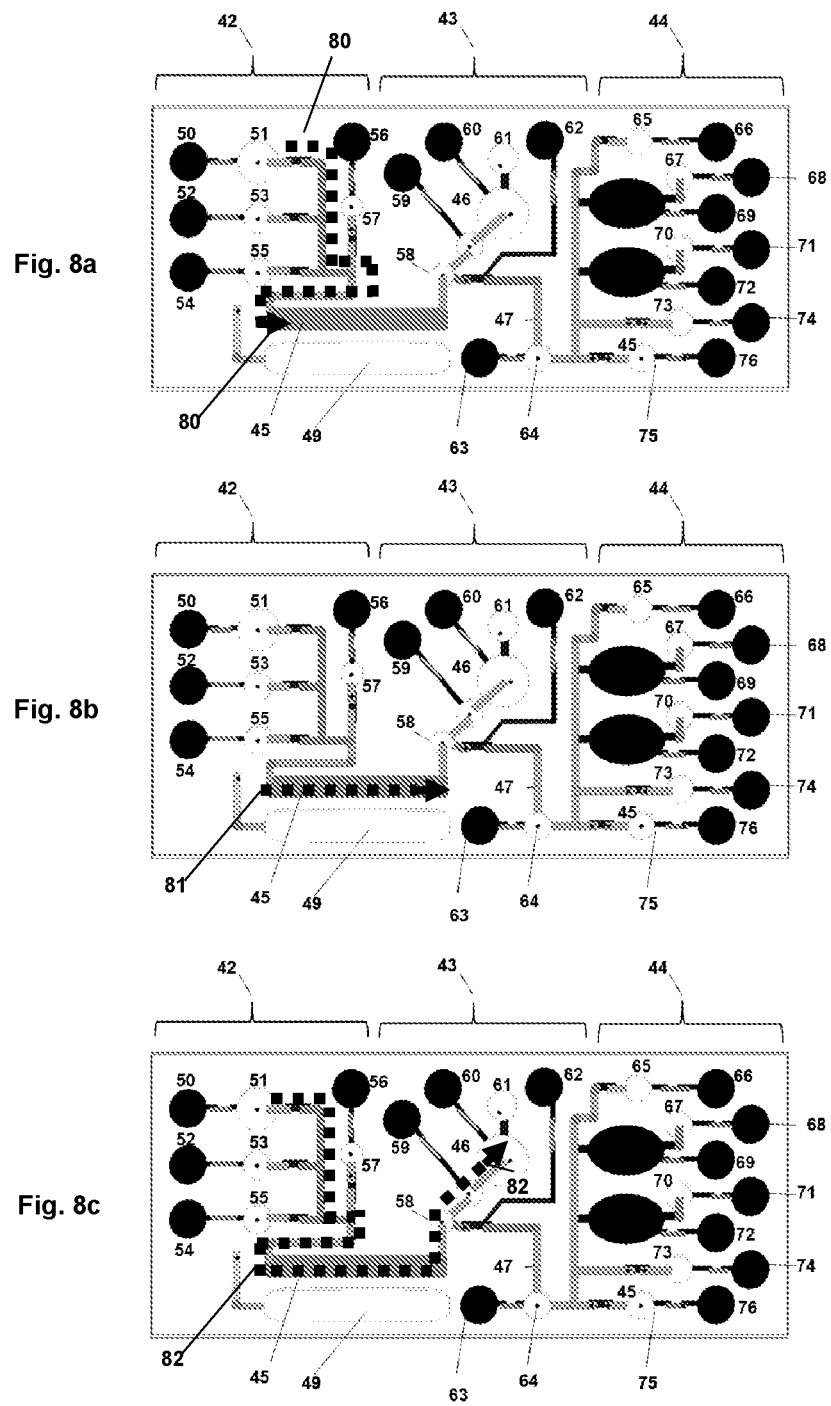
Figures 8D, 8E:
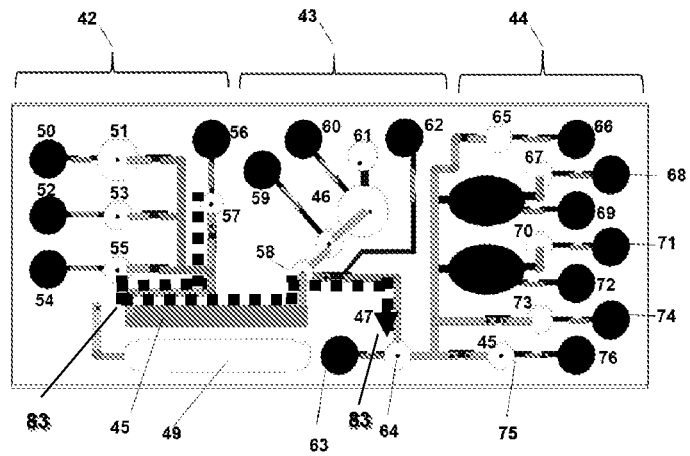

FIG. 5B is a photograph of the electronic printed circuit board manufactured to provide contacts to the electrodes of the electrolytic pumps and electronic control of the microfluidic device in 5A;

FIGS. 6A, 6B and 6C are photographs of the bottom side of the microfluidic device of one of the embodiments, manufactured based on the design shown in 5A, and showing different stages of fluidics control through balancing pressures and active flow resistance on the device;

FIGS. 7A, and 7B are photographs of the microfluidic device in FIG. 6 showing a fluid control and advancements through the array detection on the opposite, top side of the cartridge shown in FIG. 6;

FIGS. 8A, 8B and 8C are pictorial schematics of a manufactured microfluidic device, a cartridge for the performance of in-vitro diagnostic testing for sample-to-answer analysis of DNA, RNA or protein testing shown in FIG. 7, indicating flow sections that were used to experimentally quantify the flow through different sections on the cartridge;

FIG. 8E shows a table of quantitative results for fluid flow through different flow sections and pathways on the microfluidic cartridge shown in FIGS. 5,6,7, 8A-8D, performed at 3 levels of current control applied to electrolytic pumps.

FIG. 9 shows an example of a script language program developed to operate and control the sample-to-answer protocol for in-vitro diagnostics on the microfluidic device shown in FIGS. 5-8; an experimental case for controlling the operation of the microfluidic device at 80 mA is shown.

Figure 10:
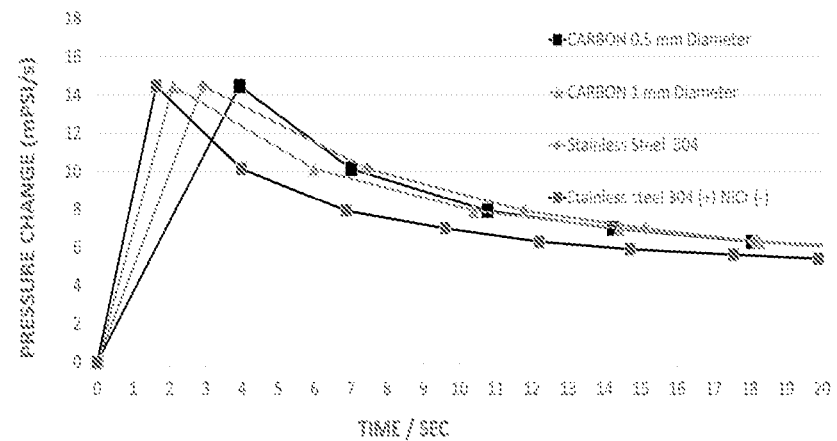

FIG. 10 is a graphical presentation of the data demonstrating a comparison of the pressures developed in the microfluidic device of the invention during its operation and using different types of sacrificial electrodes for electrolytic pumping.

Figure 11:
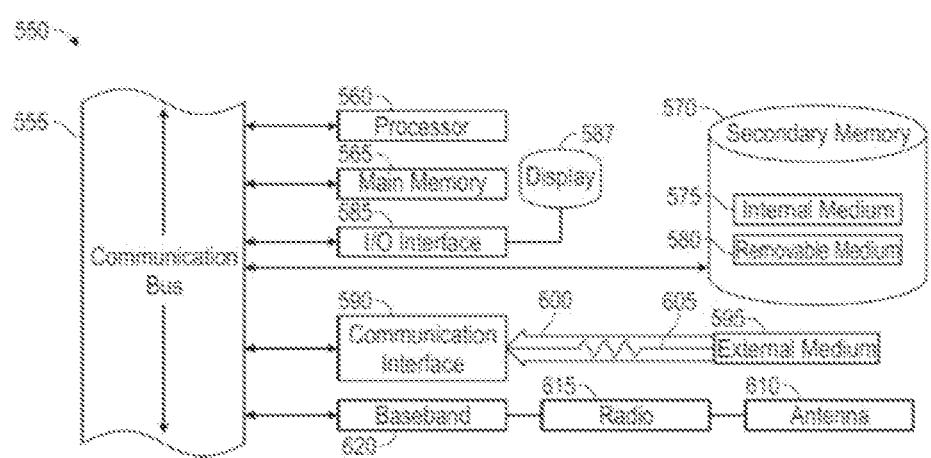

FIG. 11 is a block diagram illustrating an example wired or wireless processor enabled device that may be used in connection with various embodiments described herein.

DETAILED DESCRIPTION

The subject matter of the present invention now will be described more fully hereinafter with reference to the accompanying drawings, in which some, but not all embodiments of the subject matter of the present invention are shown. Like numbers refer to like elements throughout. The subject matter of the present invention may be embodied in many different forms and should not be construed as limited to the embodiments set forth herein; rather, these embodiments are provided so that this disclosure will satisfy applicable legal requirements. Indeed, many modifications and other embodiments of the subject matter of the present invention set forth herein will come to mind to one skilled in the art to which the subject matter of the present invention pertains having the benefit of the teachings presented in the foregoing descriptions and the associated drawings. All illustrations of the drawings are for the purpose of describing selected versions of the present invention and are not intended to limit the scope of the present invention. Therefore, it is to be understood that the subject matter of the present invention is not to be limited to the specific embodiments disclosed and that modifications and other embodiments are intended to be included within the scope of the appended claims.

Microfluidic System Based on Active Control of Flow Resistance in Microfluidic Channels and Methods of Use Thereof The present invention uses an active control of the resistance in one or more fluidic channels applied during the operation of the microfluidic device achieved with no mechanical moving elements. The passive resistance in the channels is first embedded into the microfluidics device design and during filling and packaging of the device in such a manner that the solutions, e.g., reagents and pressure-generating fluids are introduced and sequestered within the reagent chambers that cannot intermix, not using mechanical barriers but are in open communication between them through thin liquid or gas channels. These establish an initial passive resistance to flow in the channels that does not allow mixing of reagents between the reagent chambers in a packaged device, during no operation periods, such as storage.

During the operation of the device, an active control of the flow resistance in the fluidic channels is achieved by controlling the pressure in one or more fluidic channels, connected to one or more pressure producing chambers using means of generating a pressure with no mechanical moving elements, such as but not limiting to pressure generation using electrolytic gas evolution, thermal heating, catalytic heating or ultrasonic cavitation. One or multiple such pressure producing chambers are interconnected with the reagent chambers and fluidic channels, and the pressures are balanced to achieve the fluid movement in the desired direction. Multiple pressure-generating chambers can operate in parallel and the pressures are balanced or counter-balanced to overcome the passive resistance in the channels and achieve a flow control and direct the flow in the desired direction between the chambers. The flow control enables moving the fluid back-and-forth between the chambers, moving the fluid simultaneously in multiple parallel channels or chambers, or serially between the reagent, sample, sample preparation, detection, waste chamber, or any other chamber in the device with a particular use.

The control of the pressure-generating chambers can be established typically using electric contacts to electrodes, heaters or ultrasonic piezo-elements that are easily programmable using an interface and computer on the instrument controlling the microfluidic device. Once the software fluidic protocol for the activation of the pressure-generating chambers is established, typically consisting of controlling the current and time of activation of each pressure-generating actuator in the pressure-generating chamber, a reproducible flow pattern can be implemented in each disposable microfluidic device.

The microfluidic system of the invention does not require fluidic lines between the cartridge or disposable device and the instrument operating the microfluidic device or cartridge or storage of fluids in the instrument. All the relevant fluids, e.g., sample introduced into the cartridge, reagents for performing chemical or biochemical reactions for extraction and separation of the analyte in the sample preparation step, amplification of the analyte for detection, pressure-generating fluids are embedded within the device housing. This enables performance of the fluidic operations in the applications that involve the use of chemically or biochemically toxic reagents or samples, and preventing harming the user or the environment.

The manufacturing of the device, packaging of the device, the pressure generation actuators, the embedded reagents and operation of the device of the invention can be manufactured using low cost and easily scalable or robotized systems, e.g., using molded parts, screen-printed electrode actuators that assure low cost production of the device for, but not limited to the use in-vitro diagnostics.

Another aspect of the invention provides a microfluidic system based on active control of flow resistance in microfluidic channels and an improved method for microfluidic devices and disposable cartridges for use in, but not limited to the use in in-vitro diagnostics.

Accordingly, in one embodiment, a microfluidic system based on active control of flow resistance in microfluidic channels is provided, comprising:
- a) a microfluidic device comprising a housing, wherein the housing comprises a top end and a bottom end;
- b) a plurality of reagent chambers and a plurality of pressure-generating chambers, wherein the reagent chambers and the pressure-generating chambers are positioned in the housing, and wherein:
  - i) the pressure-generating chambers produce a pressure-generating fluid using no mechanical moving parts;
  - ii) the reagent chambers are connected by at least one gas channel at the top end of the housing to at least one of the pressure-generating chambers; and
  - iii) the reagent chambers are connected by one or more liquid channels at the bottom end of the housing to one or more of the pressure-generating chambers;
- c) a top substrate enclosing the pressure-generating fluid chambers, wherein the top substrate comprises fluidic channels connecting the pressure-generating chambers to one or more vent holes, thereby enabling movement of one or more reagent fluids in the one or more liquid channels at the bottom end of the housing; and
- d) a bottom substrate enclosing the reagent chambers;

wherein the movement of the one or more reagent fluids is enabled by activating the one or more pressure-generating chambers to pump the pressure-generating fluid toward the one or more reagent chambers and controlling and balancing pressure of the pressure-generating fluid to achieve active flow resistance resulting in the movement of the one or more reagent fluids in a desired direction; and wherein the microfluidic system is configured to achieve passive flow resistance during filling of the microfluidic device with the pressure-generating fluid to prevent mixing of the pressure-generating fluid with the reagents when the microfluidic system is not in operation. In some embodiments, achieving passive flow resistance during filling of the microfluidic device comprises the steps of:
- aa) filling the plurality of pressure-generating chambers with pressure-generating fluid;
- bb) enclosing the housing and the plurality of pressure-generating fluid chambers, the gas channels, and the plurality of reagent chambers with the top substrate such that the fluidic channels make desired connections between the chambers and vent holes enabling movement of one or more reagent fluids in liquid channels at the bottom end of the housing; and
- cc) inverting the microfluidic device and filling the plurality of reagent chambers with the one or more reagent fluids and enclosing the reagent chambers, the one or more reagent fluids, and the liquid channels with a bottom substrate at the bottom end of the housing.

Each reagent chamber may be connected to at least one or more pressure-generating chambers enabling balancing of pressures in fluidic channels, thus actively controlling the resistance to flow in fluidic channels, and by controlling intensity and timing of the pressure generation in operating pressure-generating chambers. This results in directing the fluid through desired channels or reagent chambers and in a desired direction. Actuating particular pressure generation actuators, by, e.g., starting the electrolysis in one or more pressure-generating chambers within pressure-generating fluid and producing and moving a pressure-generating fluid (e.g., gas, liquid, or oil) at a controlled voltage or current applied through the electrodes embedded in the pressure generation chamber, can define the fluidic protocol to operate multiple fluidic steps in the microfluidic device.

Additionally or alternatively, one or more fluids can be moved simultaneously, in parallel, or in a series of fluidic steps within the housing of the microfluidic device. This is achieved by activating pressure generation actuators, e.g., initiating electrolysis in one or more pressure generation chambers and controlling the intensity of gas evolution and timing of evolution. According to basic Faraday and Nernst equations of electrochemical splitting of water (or other pressure-generating fluid), the current applied on electrodes is proportional to the number of moles of gas produced which is further proportional to the pressure of gas produced. A very small amount of water can produce large volumes of pressurized electrolytic gas, e.g., 1 mol of water, or 18 g or 18 mL of water produce 22.4 liters of gas (in accordance with the Ideal Gas Law). This enables just a few hundred microliters of pressure-generating fluid stored in pressure-generating chambers to produce large amounts of pressurized gas with enough volume to run microfluidic device operations for a long time. Pressures of up to several hundred psi can be produced electrolytically, depending on the fluidics design, the chamber and channels geometry in the device, and current intensity applied within an operation time of the microfluidic device.

The same electrolytic actuation of pressure generation provides an option to produce minute quantities, and pressures, of gas, thus enabling a very slow and highly controlled movement of fluids in the channels or reagent chambers. Such slow, precise flows are useful in controlling slower reactions in chemical and biochemical applications of the microfluidic device, for instance, but not limited to sample preparation or analyte detection using controlled movement between analyte target and detector, or in dispersion and concentration of beads, including magnetic beads in the fluidic channels.

In some embodiments, the microfluidic system further comprises an automated electronics interface and software control configured to control and balance the pressure of the pressure-generating fluid, wherein the automated electronics interface and software control is programmed to execute a reproducible protocol for operation of the microfluidic device. The computerized control of the actuators producing pressure in different regions of the microfluidic device and establishing protocols for applying varying pressures in multiple pressure reagent chambers and balancing pressures so that the resistance to flow in fluidic channels is actively controlled may be essential in reproducibly operating fluidic protocols in disposable cartridges.

In some embodiments, the pressure-generating fluid may comprise at least one or more liquid, oil, gas, or air fluids. The pressure-generating fluid, for instance salty water in the electrolytic actuation of pressure, can be oil, lighter or heavier than water that is pushed into other channels of the microfluidic device of the invention to modify the resistance to flow in the channel and act as a valving mechanism where fluid flow in such higher resistance oil filled channel will be prevented, and allowed in a channel of lower resistance. The active control of resistance includes increasing a resistance to flow in a particular channel where gas or air pressure-generating fluids are pumped into liquid fluidic channels generating bubbles between the reagent chambers and actively affecting the flow resistance in said channel, further providing means of valving or flow control. Especially in a Y shaped design of fluidic channels, where a decision is needed in which direction the fluid should flow, exiting through the Y channel split, the injection of a different fluid phase, such as a gas into liquid, or oil into liquid, an accurate control or resistance is achieved in this manner and can be used to direct a first fluid from one reagent chamber exiting left in the Y design, and a second fluid from a different reagent chamber exiting right into a different section of the fluidic chambers in the microfluidic device of the invention. Such splitting of channels is useful for instance when sample preparation or detection processes are performed in the analytical, diagnostics applications of the microfluidic device of the invention, where washing solutions are sent into a waste chamber, and eluent or detection, analyte solution over a detection chamber or sensor.

In some embodiments, the pressure of the pressure-generating fluid ranges from about 0.1 psi to about 1,000 psi, particularly from about 0.1 psi to about 100 psi. It is appreciated by a person of ordinary skill in the art that the actuation mechanisms for generating pressure and fluid movement in pressure-generating chambers and fluidic channels described hereinabove may be used in the microfluidic device of the invention using one mechanism or a combination of different actuation mechanisms to more efficiently or precisely control the balancing of the pressures and actively controlling resistance to flow in fluidic channels and directing the fluid flow in a desired direction. Some of the actuation mechanisms may produce lower pressures, others higher, and their combination on the microfluidic device will depend on the application and specifications of the fluid velocities needed in the microfluidic device or system of the present invention.

In some embodiments, the pressure of the pressure-generating fluid in the plurality of pressure-generating chambers is generated using electrolytic gas evolution. In some embodiments, the pressure of the pressure-generating fluid in the plurality of pressure-generating chambers is generated using thermal heating, catalytic heating, ultrasonic means, electrophoretic means, or dielectrophoretic means.

Accordingly, there is further provided in accordance with yet another embodiment of the present invention a microfluidic device wherein actuation of a pressure in said pressure-generating chambers is generated using thermal heating, utilizing electrodes or coils position directly within the pressure-generating fluid, or heaters including, but not limited to screen-printed inks at the bottom substrate of the housing, in locations where heating or pressure generation is desired, such as in pressure-generating chambers. Typically, highly conductive screen-printed, meandering coils, based on conductive silver inks can be printed on pressure sensitive adhesive and bonded to the bottom substrates of the device housing. The contacts to these heating elements may be provided directly by contacting the silver ink printed lines at the edge of the device housing using spring loaded pogo-pins, or inserting the housing with printed silver ink contacts into a terminal located within the instrument or microfluidics controller. Alternatively, a simple, low cost, printed circuit board (PCB) with copper lines can be attached to the bottom of the housing of the device where either pin contacts or screen-printed conductive lines are pressed with the PCB board. The contact to the PCB board and contact lines are made using standard electronic terminals located in the instrument or microfluidics controller.

There is also provided in accordance with another embodiment of the present invention a microfluidic system based on active control of flow resistance in microfluidic channels wherein actuation of a pressure in said pressure-generating chambers is generated using catalytic heating, utilizing hydrogen gas produced electrolytically in the pressure producing chamber and passing the hydrogen over a miniature catalytic converter, where catalyst chosen from, but not limited to Pt, Pd, particles or deposits is made on a ceramic substrate. The size of such catalytic converter is preferably 1-20 mm. the hydrogen gas passing over the catalyst heats up the ceramic insert in the housing of the microfluidic device and rapidly generating the heat, and subsequently the vapors created generate pressure in the fluidic channel. Such catalytic heating using hydrogen passing over the miniature catalytic converter can heat the miniature ceramic element to 600 C within only 3-5 seconds. The temperature is controlled by the amount of hydrogen produced electrolytically, which is further controlled electronically by adjusting the current or voltage on the electrolytic electrodes in the pressure-generating chamber.

In accordance with yet another embodiment of the present invention, a microfluidic system based on active control of flow resistance in microfluidic channels wherein actuation of a pressure in said pressure-generating chambers is generated using ultrasonically created pressure. The pressure is generated using ultrasonic piezoelectric transducers that under an applied high-frequency alternating voltage pulses contract or expand generating mechanical vibrations that serve as pressure generation for movement of fluids in the fluidic channels or reagent chambers of the present invention. Typically artificially manufactured piezoelectric materials such as, but not limited to Polyvinylidene difluoride, PVDF or PVF2, Barium titanate, Lead titanate, Lead zirconate titanate (PZT), Potassium niobate, Lithium niobate or Lithium tantalate are used as piezoelectric elements activated by electrodes in contact with the piezoelectric material.

In some embodiments, electrolytic gas evolution generates the pressure of the pressure-generating fluid by electrolysis of the pressure-generating fluid, wherein the pressure-generating fluid comprises water, an inorganic salt solution, or a conductive organic solution, and wherein electrolysis of the pressure-generating fluid produces a gas comprising oxygen, hydrogen, and/or chlorine. For example, an electrolytic generation of gases, like oxygen and hydrogen generated from electrolysis of aqueous, particularly salt solutions, may be used as a pressure-generating fluid in pressure-generating chambers to pressurize the fluid in reagent chambers and fluidic channels and move the fluid of interest, from one reagent chamber to another, in a desired direction. The desired direction may include back-and-forth movement of one or more fluids of interest in the microfluidic device, enabling mixing between reagents in different reagent chambers.

Accordingly, in another embodiment, pressure-generating fluids other than water, but not limited to salt solutions are used, e.g., containing chlorides, carbonates or other salts that will produce gases in addition or other than oxygen and hydrogen from water splitting. Thus, chloride solutions will produce chlorine gas, carbonate solution carbon dioxide at lower pH, and other reactions known in the art that could be utilized to generate gases useful not only in controlling pressures in the fluidic channels but actively controlling reactions in channels or chambers. Such embodiments of the present invention that include active, or on demand production of reactant gases, or reactants for controlling reactions in reagent chambers, may include, but are not limited to, controlling pH in reagent chambers, through using anolyte and catholyte solution from pressure pumping chambers and fluids, that generate acidic (where oxygen is evolved) or basic (where hydrogen is evolved) solutions or reactant that can adjust a pH in the reagent chamber, or chlorine for disinfection of the device, e.g., post-using steps that involve infectious agents in the device, or oxygen to control aerobic growth of cells, pathogens, or organoids, or carbon dioxide to control anaerobic growth of cells, pathogens, or organoids in the various applications of the fluidic device and system of present invention.

In some embodiments, the microfluidic device is configured to control the pressure of the pressure-generating fluid electronically using electrodes, electronic contacts, and/or switches embedded in the housing.

In some embodiments, the microfluidic system further comprises one or more electrodes for electrolytic gas evolution, wherein the one or more electrodes comprise anodic corrosion-stable noble metal electrodes or one or more anodically sacrificial electrodes, wherein the one or more anodically sacrificial electrodes comprise stainless steel, aluminum, copper, carbon, carbon inks, plated electrodes, and/or screen-printed electrodes.

In some embodiments, the microfluidic system is configured to enable the gas produced by electrolysis to control pH and/or conductivity reactions in the one or more of the plurality of reagent chambers.

In some embodiments, the one or more vent-holes are embedded within the top substrate of the housing atop one or more pressure-generating chambers or one or more reagent chambers.

In some embodiments, the one or more reagent fluids comprise aqueous or non-aqueous liquids comprising one or more reagents for extraction, amplification, or detection of one or more analytes comprising one or more biomarkers, nutrients, and/or chemicals. The reagent fluids may comprise any sample that comprises one or more biomarkers, nutrients, and/or chemicals, such as an analytic sample, clinical sample, and the like. The one or more biomarkers may comprise any nucleic acid (DNA or RNA), protein, or fragments thereof. The one or more chemicals may comprise: chemicals for analyte extraction, amplification, and/or detection, chemicals useful in controlling fluids in microfluidic devices or cartridges; nutrients for controlling growth of cells, pathogens, and/or organoids (e.g., including but not limited to tissue engineering or cloning processes); chemicals as reagents for generating inorganic and organic compounds (e.g., including but not limited to inorganic crystals or protein crystallization); and/or chemicals for generating nano-compounds or nano-elements (e.g., including but not limited to carbon nanotubes, nanofilaments, and/or graphene compounds).

In some embodiments, the microfluidic system further comprises one or more gas permeable membranes atop the plurality of pressure generation chambers, wherein the one or more gas permeable membranes separate liquid and gas pressure-generating fluids in the pressure-generating chambers while allowing permeation of pressure-generating fluid into the fluidic channels without mixing between the pressure-generating fluid and the one or more reagent fluids in the plurality of reagent chambers.

In some embodiments, the microfluidic system is configured to pump the pressure-generating fluid toward one of the plurality of reagent chambers that comprises one of the vent holes, or wherein the pressure-generating fluid is pumped toward one of the plurality of pressure generation chambers that comprises a vent hole, thereby causing a high flow velocity and generating a Venturi vacuum, wherein the Venturi vacuum enables control of fluid flow resistance and/or fluid flow velocity.

Reference is now made to FIGS. 1A and 1B which are a simplified exploded view illustration of the microfluidic device constructed and operative in accordance with a embodiment of the present invention and FIG. 1B is a cross section of the housing of the device where simple back-and-forth pumping is demonstrated between two reagent chambers.

As seen in FIGS. 1A and 1B, microfluidic device of the embodiment comprises a housing 1, having a top end 2 and bottom end 3, is enclosed with a top substrate 15 and a bottom substrate 16. The housing 1, accommodates reagent chambers, where a sample is added into chamber 4, connected through a gas channel 18 to a pressure generation chamber 9, and reagent 1 in chamber 5 that is connected through a gas channel 19 to a pressure generation chamber 10. The sample chamber 4 and reagent chamber 5 are connected only through liquid line 22 at the bottom end 2 of the housing. The pressure-generating chambers 9 and 10 comprise pressure-generating fluid 13 that typically is a salt containing water to promote electrolysis. Pressure-generating fluid 14, typically oxygen and hydrogen gas, produced during electrolysis expand in pressure direction line 26 through gas channel 18 or in pressure direction line 28 through gas channel 19. The pressure developed during electrolysis in both pressure-generating chambers 9 and 10 is controlled by adjusting current, and/or voltage on the electrode 28 protruding from the bottom end of housing 3. Typically, noble metal electrodes could be used to prevent a dissolution of anode (connected to a positive pol of the voltage control). However, platinum and noble metal electrodes are too expensive to be used in a disposable, low cost microfluidics devices, and the low cost, but not limited to stainless steel, carbon electrodes, or screen-printed electrodes, are preferred in the embodiments of the invention. Since the timing of the operation of the microfluidic device is limited, testing was performed that confirmed that these electrodes remain stable within the time of the operation of the device, and no effect on analytes or their testing was observed from the dissolution products from the anodes tested. The embodiment of the invention shown in FIGS. 1A and 1B comprises vent holes 17 in both pressure-generating chamber 9 and 10. The fluidics design of the vent hole size, the geometry of the gas and liquid channels, volumes of reagents, and the need for embedding meandering channels, or channels that will provide even more resistance to flow when those are going or led from bottom end 3 to top end 2 of the housing or vice-versa, are all part of the fluidic pre-design that incorporates passive resistance elements into the microfluidic device design. This passive flow resistance in each channel remains the same after microfluidics device manufacturing. Once the device or cartridge is put into operation, by actuating electrodes in pressure-generating chambers, the current intensity and timing of actuation needs to be optimized to achieve the flow in a desired direction. Example in FIGS. 1A and 1B demonstrates a simple flow control between only 2 chambers, sample chamber 4 and reagent chamber 5. Since both pressure generation chambers 9 and 10, contain vent holes 17, to push the sample in chamber 4 (that was for instance introduced into chamber 4, containing a lysis buffer, e.g., for initiating analyte extraction in the sample preparation step) into chamber 5, the pressure, thus the current applied on electrodes in pressure generation chamber 9 needs to be higher than in pressure generation chamber 10. This will result in emptying sample chamber 4 in direction of the pressure direction line 27 through liquid channel 22 connecting the reagent chamber 5 at the bottom end 3 of the microfluidic device housing 1. A counter-pressure formed in pressure chamber 10, exercised through gas channel 19 and in direction of the pressure direction line 28 can be used to control the flow velocity in channel 22. If needed, the solution now in reagent chamber 5 could be pushed back to chamber 4, or back-and-forth between those chambers, to achieve mixing of the solution (sample) in chamber 4 and reagent chamber 5. This arrangement of the balanced pressures using localized pressure generation (9 and 10), connected to any reagent chamber on the microfluidic device (here 4 and 5 are connected), and existence of vent holes in adequate places, enables high flexibility of fluid flow control in any direction on the microfluidic device, and between any reagent chamber embedded in microfluidic device housing 1. The protocol of actuation of electrodes, based on current intensity and time of actuation of each pressure-generating chamber and balanced pressures in each fluidics step on the cartridge needs to be pre-tested and established for a particular application of the microfluidics device. This accounts for differences in manufacturing but provides a common protocol to reproducibly run any number of cartridges manufactured in the same way.

Reference is now made to FIGS. 2A-2D, which are simplified illustrations of cross section (A-A') of the microfluidic device in FIG. 1, showing establishment of a passive resistance in flow channels utilizing a specific protocol of filling of the microfluidic device of the invention so that the fluids in pressure-generating chambers 9 and 10 cannot mix with useful fluids in reagent chambers 4 and 5. This presents a critical part of the invention, that is taken first into account during the design of the microfluidics device, by designing the appropriate geometry of the fluidic channels, e.g., embedding passive resistance elements of predictive fluidic behavior, such as meandering channels with controlled length, up and down insertion of small holes into a channel that generates relatively high resistance to flow in a particular channel, and can be controlled by the diameter of the hole. The width, depth and shape of the channels and chambers, as well as varying channels with enlargements in width could be used to control burst pressures from the channel into a chamber or into any such enlargements. This static flow resistance situation in the entire microfluidic device presents an initial step to establish a reproducible passive resistance within the cartridge and between the cartridges manufactured serially. FIGS. 2A-2E demonstrate a specific protocol of filling such cartridge with established passive flow resistance to further avoid and prevent any mixing between the reagents A and B, and/or reagents and pressure-generating fluid 13 in pressure-generating chambers 9 and 10. It is important to note that reagents and pressure-generating fluid are in communication through gas channels 18 and 19, with no physical or mechanical barrier between them. The flow in gas channels 18 and 19, or through liquid channel 22, connecting two reagent chamber 4 and 5 is prevented using the following packaging and filling protocol of the cartridge. Bottom substrate 16, containing fluidic channels, or alternatively a cartridge with molded in channels and covered with a pressure sensitive adhesive, is first attached to the housing 1 at bottom end of housing 3. Pressure-generating fluid A, typically a salt solution, for instance, but not limited to potassium nitrate or phosphate solutions (preferably 1.0 M-3.0 M), is first filled into pressure-generating chambers 9 and 10, which can be performed using robotized filling. In FIG. 2B, substrate 15, containing gas channels and preferably enclosed with pressure sensitive adhesive, encloses the top end 2 of housing 1. The microfluidic device is then turned upside down (cf., FIG. 2C), so that the substrate 16 is not on top and substrate 15 on bottom. Since the channels 18 and 19 are designed with high passive resistance to flow, that can be further enhanced by using hydrophobic materials, or coatings, for substrates 15 and 16, pressure-generating fluid 13 cannot flow from the pressure-generating chambers 9 and 10, and remain sequestered in those chamber since external air pressure is higher than in the chamber. Reagent solutions A and B are now filled into reagent chambers 4 and 5, respectively. Top substrate 15 (a second piece of same substrate covering reagent chambers) is mounted now on top end 2 or the housing 1, enclosing reagent chambers. This structure and the filling protocol assure no mixing of any fluid in the enclosed fluidic device of the invention. The channels are open, the chambers can communicate through thin gas or liquid channels, but the flow between them is prevented due to too high flow resistance established in this initial stage of achieving high passive resistance in channels that cannot be overcome in the packaged device without and/or generating and increasing pressure internally.

FIGS. 2E and 2F are simplified illustrations of cross section (A-A') of the microfluidic device in FIG. 1, further showing the steps of actuating the microfluidics device of one of embodiments, packaged in accordance to the protocol shown in FIGS. 2A-2D. Details of the microfluidic device components and actuation are shown in FIG. 1B, and FIGS. 2E and 2F show the same actuation process but in 2 steps. First, FIG. 2E shows emptying of the reagent chamber 4, or the sample chamber, and secondly, FIG. 2F shows filling of chamber 5 under the same condition as applied in FIG. 1A. The pressures balanced by pressure chambers 9 and 10 regulate the movement of the fluid in a desired direction from reagent chamber 4 to reagent chamber 5.

Reference is now made to FIGS. 3A and 3B which are a simplified exploded view illustration of the microfluidic device constructed and operative in accordance with a embodiment of the present invention and FIG. 1B is a cross section of the housing 1 of the device with multiple reagent chambers 4,5,6,7 and 8 connected with pressure generation chambers 9,10,11 and 12 to further demonstrate localized balancing of pressures and active control of resistance in flow channels to achieve more complex fluidic control including valving, such as in Y split of fluidic channels 23 entering the Y split and 24 and 25 exiting the Y split. The control of pressures in said liquid channels is explained through pressure direction lines 28, 32, 33, 34, 35, 36 and 37. The function of the microfluidics device 1 shown could be easier understood if an application such as sample preparation and detection on the cartridge is envisioned and is described hereinbelow in detail. First, a sample is added to chamber 4, that is then enclosed with a cap to hermetically close the device. All reagents are pre-filled as described hereinabove in FIGS. 2A-2D. Chamber reagent 4 may already contain a lysis buffer to extract the analyte, DNA, RNA or protein from the cells or pathogens in the sample. Pressure-generating chamber pushes the sample from chamber 4 into chamber 5 along the pressure direction lines 26 and 27. If it is desired to fill the reagent chamber 5 with the sample, counter pressures from pressure-generating chambers 9, 11 and 12 are applied to prevent the flow out of chamber 5 through the exiting liquid line 23 positioned at the bottom end 3 of housing 1. The sample 4 mixed with lysis buffer in chamber 4, both now in chamber 5, could be pushed back-and-forth between chambers 4 and 5 to enhance the analyte extraction. The solution in chamber 5 can be pushed further toward the Y split using pressure chambers 9 and 10 and minimizing pressure in pressure chambers 11 and 12. The example of a Y split may be useful, for instance if multiple reagents chambers are used in a magnetic bead based analyte extraction, where multiple washing solutions are used for bead washing. Washing solutions are directed through the Y split through the chamber 6 into the waste chamber 7. The eluent buffer is than passed over the beads, for instance kept within the chamber 5 or 6 by bringing a magnet close to microfluidic device housing 1. The eluent is directed toward chamber 8, that can contain a sensor or toward further chambers and reagents to achieve detection. The detection protocols often require bringing reporter solutions and washing solutions. It is envisioned that various detection principles can be embedded within the cartridge to achieve accurate analyte sensing. In one of the embodiments, the microfluidic principles of the present invention enable embedding multiple sample preparation and/or detection processes, yielding a single cartridge with dual or multiple detection of various analytes, for instance simultaneous detection of RNA, DNA, proteins or other analytes. This multiplexed analytical method performed in a single analysis will increase accuracy of disease detection and provide timely guidance for therapy.

Reference is now made to FIGS. 4A and 4B, which are photographs of a manufactured microfluidic device of the invention, 4A showing the top view of the microfluidic device, cartridge, and 4B bottom view of the same cartridge, where 4C present an insert from the photograph in 4B showing a closeup of a electrolytic pump. Although many other applications of the present invention will be understood for those skilled in the art, the device in FIG. 4 shows one embodiments for performing analyte detection in in-vitro diagnostics. Section 42 shown on the cartridge comprises chambers and fluidic channels to perform sample preparation, section 43 is a transition from sample preparation to detection 44. The sample preparation chamber 45 is made longitudinally for instance, to enhance the magnetic separation. Chamber 46 is one of the waste chambers, and hole 47 through the housing 1, makes fluidic connection to the array 48 located on the other side of the cartridge and shown in FIG. 4b.

FIG. 5A illustrates a pictorial schematic of a manufactured microfluidic device of another embodiment of a microfluidic device serving as a cartridge for the performance of in-vitro diagnostic testing for sample-to-answer analysis of DNA, RNA or protein testing on a single cartridge. The cartridge is manufactured mechanically, although other methods can be used to manufacture a low cost, mass production device, e.g., using molding and attachment of pressure sensitive adhesive covers. The pressure in the sample chamber 51 is controlled by pressure-generating chamber 50, wash1 chamber 53 by pressure-generating chamber 52, wash2 chamber 55 by pressure-generating chamber 54, eluent chamber 57 by pressure-generating chamber 56, pressure-generating chambers 59 and 60 are pumps for resistance control in waste chamber 46 and waste overflow chamber 61, as well as providing active resistance control on the Y split 58. Transition from the sample preparation to detection at the entrance 47 toward array 48, is controlled by pressure-generating chamber or pump 63 and pressure chamber 64. The detection side is operated and controlled through ligation chamber 65 and its pressure-generating chamber or pump 66, amplification reagent chamber 67 with pump 68, reporter chamber 70 with pump 71, reporter wash 1 73 with pump 74, and reporter wash 2 75 with pump 76. Pumps 69 and 72 are used for additional active resistance control in detection fluidic channels and/or for hydration of lyophilized enzyme reagents in wider chambers shown with pumps 69 and 72.

It will be appreciated by persons skilled in the art that many other and flexible fluidics network arrangements of reagents, pressure-generating chambers and other fluidics elements can be embedded in embodiments of the present invention yielding other applications that can replace chemical or biochemical operations in laboratories including, but not limited to diagnostics, cell or pathogen culturing, tissue and protein engineering, miniaturized chemical and electrochemical reactors engineering.

FIG. 5B is a photograph of the electronic printed circuit board (PCB) manufactured to provide contacts to the electrodes of the electrolytic pumps and electronic control of the microfluidic device in 5A. Such connector board is one of the low cost approaches to provide efficient contacting to the electrodes in pressure generation chambers (as low as <1$ per such contactor PCB can be economized, if large scale production is envisioned). The insert in FIG. 5B shows electrodes embedded within the pressure-generating chamber.

Reference is now made to FIGS. 6A-6C, which are photographs of operation of a manufactured microfluidic device of one of embodiments of the invention. FIGS. 6A, 6B and 6C are photographs of the bottom side of the microfluidic device design shown in 5A, and showing different stages of fluidics control through balancing pressures and active flow resistance on the device.

FIGS. 7A, and 7B are photographs of the microfluidic device in FIG. 6 showing a fluid control and advancements through the array detection section on the opposite, top side of the cartridge shown in FIG. 6;

As will be described hereinbelow in detail, each of the photographs in FIGS. 6 and 7 present fluid advancement during the operation of microfluidic device of one of embodiments of the invention. The timing of the fluid advancement was measured in each section to quantify the operation of the device and analyze the operation of the fluidics control, as shown in FIG. 8. FIG. 6A shows transfer of the fluid from sample chamber 51 using pressure generation chamber 50 and balancing with pressure chamber 52, 54 and 56 if necessary, into sample preparation chamber 51. In FIG. 6B, the fluid advancement is clearly shown through the fluidic channel pathway from sample chamber 51 to sample preparation chamber 45 where the fluid is emptied from chamber 51. The fluid continues from sample preparation chamber 51 toward the Y split 58 and is directed into waste 46, by operating the pumps 51, and 63 and using a pressure resistance adjustment chamber 64, through balancing their pressure by controlling the current applied to the electrodes in their respective pressure-generating chambers. The fluid advancement shown in FIG. 6B clearly shows movement of fluid in a desired direction, toward and filling the waste chamber 46, and leaving the detection fluidic channels empty, by adjusting of pressures locally on the other side of the Y split 58 exit toward the detection side.

FIG. 6C shows the subsequent fluidic pathway where the eluent from eluent chamber 57, operated by electrolysis pump 56, passing toward the Y split 58 and entering the detection side of the Y split, avoiding transport into the waste 46. This is achieve by balancing pressures at pumps and chamber resistance elements 56,59,60,63 and 64, and directing the fluid into the hole 47 connecting one side of the cartridge to the detection array positioned on the other side of the device housing.

FIGS. 7A and 7B are photographs of the device on the array 48 side of the microfluidic device showing the advancement of the fluid through the array. FIG. 7A demonstrates filling the detection array ~75% of its volume. FIG. 7B C shows complete filling of the detection array, with no bubble in the detection window. A smooth and complete filling of the detection device is essential for, e.g., fluorescence optical detection of the signals on the array.

Reference is now made to FIGS. 8A, 8B and 8C which are pictorial schematics of a manufactured microfluidic device, a cartridge for the performance of in-vitro diagnostic testing for sample-to-answer analysis of DNA, RNA or protein testing shown in FIG. 7, indicating flow sections that were used to experimentally quantify the flow through different sections on the cartridge.

FIGS. 8A, 8B, 8C and 8D are pictorial schematics of a manufactured microfluidic device, a cartridge for the performance of in-vitro diagnostic testing for sample-to-answer analysis of DNA, RNA or protein testing shown in FIG. 7, indicating different flow sections and pathways that were used to experimentally quantify the flow through different sections on the cartridge. The pathways where the advancement of the fluid was measured by measuring the time to reach a certain point in the fluidics network are indicated by dotted lines. FIG. 8A shows a pathway 80 from sample chamber 51 to beginning of magnetic bead sample preparation, or analyte extraction chamber 45. FIG. 8B shows pathway 45 through the longitudinal chamber 45, from beginning to end of the sample preparation chamber. FIG. 8C shows pathway 82 from sample chamber 51 to waste chamber 46 and overflow 61. FIG. 8D shows pathway 83 from eluent chamber 57 to entrance to the detection array 47.

FIG. 8E shows a table of quantitative results for fluid flow through different flow sections and pathways 80,81,82, and 83 on the microfluidic cartridge shown in FIGS. 5,6,7, 8A-8D. The timing of fluid advancement was measure in and performed at 3 levels of current control, 90 mA, 200 mA and 300 mA. As expected, the timing to complete the pathways 80, 81, 82, and 83 decreased, or the flow through the pathway was increased with higher current applied. This indicated that the fluid protocols could be precisely adjusted and adapted to the needs of the processes in the cartridge, e.g., requiring potentially to slow down the flow through the sample preparation chamber, to increase the efficiency of magnetic separation. An overall short time of cartridge operation is desired, in particular if it is used in point-of-care diagnostics, where expected timing for the entire sample-to-answer process is ca 15-20 minutes or shorter. The table demonstrates that an overall sample preparation time could be controlled within 6.54 min, 4.34 min, or 2.33 min, by operating the electrolysis pumps with electrodes controlled 90 mA, 200 mA or 300 mA, respectively.

FIG. 9 shows an example of a script language program developed to operate and control the sample-to-answer protocol for in-vitro diagnostics on the microfluidic device shown in FIGS. 5-8. An electronics interface with field programmable gate array (FPGA) based electronics control and interface was designed and manufactured, and a Labview for Windows (National Instrument, Inc., USA) was used for graphical programing of the interface and control of the actuation of the electrolytic pumps. A simple script language was developed that enables the user to easily modify or optimize the actuation of the electrolytic pumps (ca. 15 pumps) positioned on different locations on the microfluidic device. An example of such script language protocol is shown in FIG. 9 for the experimental case shown in FIG. 8A-8E for controlling the operation of the microfluidic device at 80 mA.

Reference is now made to FIG. 10, which is a graphical presentation of the data demonstrating a comparison of the pressures developed in the pressure-generating chambers, or electrolytic pumps of the microfluidic device of the invention during its operation and using different types of sacrificial electrodes for electrolytic pumping. The electrolytic gas evolution used for generating pressure in one of the embodiments of the invention can be achieved using anodic corrosion stable noble metal electrodes, however those prohibitively increase the cost of the device. Other types of electrode materials were tested, especially materials that can be used as anodically sacrificial electrodes such as electrodes made of, but not limited to stainless steel, aluminum, copper, carbon, carbon inks, plated electrodes or screen-printed electrodes. Carbon-ink screen-printed electrodes demonstrated stability for operation as electrodes in the electrolytic pump up to 5-10 minutes, if operated at current lower than 80 mA. Higher currents may be needed to shorten the fluidics transport operation in the microfluidic devices, and those screen-printed electrodes will find their application in slower fluidics, or requiring small, short movements, shorter operation, or smooth slow fluidics transport in microfluidics devices. FIG. compares pressure developed from operating different types of electrodes as actuators for electrolytic pumps. A simple experimental setup, corresponding to the design shown in FIG. 1A was used in testing. The change of pressure expressed as mPSI/s is shown as a function of time of operation of the device. It may be particularly important to have higher pressures within initial short burst of pressure and within few seconds of operation of the pumps. A stainless steel 304 anode, with Ni—Cr cathode showed best performance, followed by a carbon rod of larger diameter (1 mm). It should be noted that after 15-20 s of operation under constant current control, all electrodes exhibit relatively constant pressure, and no pressure changes during the operation. This continued throughout at least 10 minutes of operation of the microfluidics device. Some anodic residues, as expected were observed, especially with stainless steel, copper, or aluminum anodes, but surprisingly, the rod or disc electrodes, at ~1 mm diameter exhibited stability during the required time of operation of the microfluidic device. The anodic product exuded into the pressure-generating chambers, involving mostly metal salts of the electrode material, although some slightly changing the color of the solution did not affect fluorescence optical detection signal background.

FIG. 11 is a block diagram illustrating an example wired or wireless system 550 that may be used in connection with various embodiments described herein. For example the system 550 may be used as or in conjunction with controlling the operation of the microfluidic device as described herein. The system 550 can be a conventional personal computer, computer server, personal digital assistant, smart phone, tablet computer, or any other processor enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 550 preferably includes a main memory 565 and may also include a secondary memory 570. The main memory 565 provides storage of instructions and data for programs executing on the processor 560. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include an internal memory 575 and/or a removable medium 580, for example a floppy disk drive, a magnetic tape drive, a compact disc ("CD") drive, a digital versatile disc ("DVD") drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 570. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the system 550.

System 550 may also include an input/output ("I/O") interface 585. The I/O interface 585 facilitates input from and output to external devices. For example the I/O interface 585 may receive input from a keyboard or mouse and may provide output to a display 587. The I/O interface 585 is capable of facilitating input from and output to various alternative types of human interface and machine interface devices alike.

System 550 may also include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored when executed, enable the system 550 to perform the various functions of the present invention as previously described.

In this description, the term "computer readable medium" is used to refer to any non-transitory computer readable storage media used to provide computer executable code (e.g., software and computer programs) to the system 550.

Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network (or otherwise described herein). The wireless communication components comprise an antenna system 610, a radio system 615 and a baseband system 620. In the system 550, radio frequency ("RF") signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570.

Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown) that are executable by processor 560.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above-described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general-purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

In other embodiments, a method is provided for actively controlling flow resistance in microfluidic channels of a microfluidic system, comprising:
a) providing a microfluidic system comprising a microfluidic device, wherein the microfluidic device comprises:
  i) a housing, wherein the housing comprises a top end and a bottom end;
  ii) a plurality of reagent chambers and a plurality of pressure-generating chambers, wherein the reagent chambers and the pressure-generating chambers are positioned in the housing, and wherein:
    aa) the pressure-generating chambers produce a pressure-generating fluid using no mechanical moving parts;
    bb) the reagent chambers are connected by at least one gas channel at the top end of the housing to at least one of the pressure-generating chambers; and
    cc) the reagent chambers are connected by one or more liquid channels at the bottom end of the housing to one or more of the pressure-generating chambers;
  iii) a top substrate enclosing the pressure-generating fluid chambers, wherein the top substrate comprises fluidic channels connecting the pressure-generating chambers to one or more vent holes, thereby enabling movement of one or more reagent fluids in the one or more liquid channels at the bottom end of the housing; and
  iv) a bottom substrate enclosing the reagent chambers; wherein the microfluidic system is configured to achieve passive flow resistance during filling of the microfluidic device with the pressure-generating fluid to prevent mixing of the pressure-generating fluid with the reagents when the microfluidic system is not in operation; and
b) activating the one or more pressure-generating chambers to pump the pressure-generating fluid toward the one or more reagent chambers and controlling and balancing pressure of the pressure-generating fluid to achieve active flow resistance resulting in the movement of the one or more reagent fluids in a desired direction, wherein the movement of the one or more reagent fluids is enabled.

In some embodiments, the method for actively controlling flow resistance in microfluidic channels of a microfluidic system comprises achieving passive flow resistance during filling of the microfluidic device, further comprising the steps of:
ai) filling the plurality of pressure-generating chambers with pressure-generating fluid;
bi) enclosing the housing and the plurality of pressure-generating fluid chambers, the gas channels, and the plurality of reagent chambers with the top substrate such that the fluidic channels make desired connections between the chambers and vent holes enabling movement of one or more reagent fluids in liquid channels at the bottom end of the housing; and
ci) inverting the microfluidic device and filling the plurality of reagent chambers with the one or more reagent fluids and enclosing the reagent chambers, the one or more reagent fluids, and the liquid channels with a bottom substrate at the bottom end of the housing.

In some embodiments, the method for actively controlling flow resistance in microfluidic channels of a microfluidic system is executed by an automated electronics interface and software control configured to control and balance the pressure of the pressure-generating fluid, wherein the automated electronics interface and software control is programmed to execute a reproducible protocol for operation of the microfluidic device.

In some embodiments of the method for actively controlling flow resistance in microfluidic channels of a microfluidic system, the pressure of the pressure-generating fluid in the plurality of pressure-generating chambers is generated using electrolytic gas evolution.

In some embodiments of the method for actively controlling flow resistance in microfluidic channels of a microfluidic system, the pressure of the pressure-generating fluid in the plurality of pressure-generating chambers is generated using thermal heating, catalytic heating, ultrasonic means, electrophoretic means, or dielectrophoretic means.

In some embodiments of the method for actively controlling flow resistance in microfluidic channels of a microfluidic system, the microfluidic device is configured to control the pressure of the pressure-generating fluid electronically using electrodes, electronic contacts, and/or switches embedded in the housing.

In some embodiments of the method for actively controlling flow resistance in microfluidic channels of a microfluidic system, the one or more reagent fluids comprise one or more reagents for extraction, amplification, or detection of one or more analytes comprising one or more biomarkers, nutrients, and/or chemicals.

In some embodiments of the method for actively controlling flow resistance in microfluidic channels of a microfluidic system, the one or more pressure-generating fluids comprise aqueous or non-aqueous liquids.

In some embodiments of the method for actively controlling flow resistance in microfluidic channels of a microfluidic system, the one or more vent-holes are embedded within the top substrate of the housing atop one or more pressure-generating chambers or one or more reagent chambers.

In some embodiments of the method for actively controlling flow resistance in microfluidic channels of a microfluidic system, the pressure of the pressure-generating fluid ranges from about 0.1 psi to about 1,000 psi, particularly from about 0.1 psi to about 100 psi.

In some embodiments of the method for actively controlling flow resistance in microfluidic channels of a microfluidic system, electrolytic gas evolution generates the pressure of the pressure-generating fluid by electrolysis of the pressure-generating fluid, wherein the pressure-generating fluid comprises water, an inorganic salt solution, or a conductive organic solution, and wherein electrolysis of the pressure-generating fluid produces a gas comprising oxygen, hydrogen, and/or chlorine.

In some embodiments of the method for actively controlling flow resistance in microfluidic channels of a microfluidic system, the microfluidic system further comprises one or more electrodes for electrolytic gas evolution, wherein the one or more electrodes comprise anodic corrosion-stable noble metal electrodes or one or more anodically sacrificial electrodes, wherein the one or more anodically sacrificial electrodes comprise stainless steel, aluminum, copper, carbon, carbon inks, plated electrodes, and/or screen-printed electrodes.

In some embodiments of the method for actively controlling flow resistance in microfluidic channels of a microfluidic system, the microfluidic system is configured to enable the gas produced by electrolysis to control pH and/or conductivity reactions in the one or more of the plurality of reagent chambers.

In some embodiments of the method for actively controlling flow resistance in microfluidic channels of a microfluidic system, the microfluidic system further comprises one or more gas permeable membranes atop the plurality of pressure generation chambers, wherein the one or more gas permeable membranes separate liquid and gas pressure-generating fluids in the pressure-generating chambers while allowing permeation of pressure-generating fluid into the fluidic channels without mixing between the pressure-generating fluid and the one or more reagent fluids in the plurality of reagent chambers.

In some embodiments of the method for actively controlling flow resistance in microfluidic channels of a microfluidic system, the microfluidic system is configured to pump the pressure-generating fluid toward one of the plurality of reagent chambers that comprises one of the vent holes, or wherein the pressure-generating fluid is pumped toward one of the plurality of pressure generation chambers that comprises a vent hole, thereby causing a high flow velocity and generating a Venturi vacuum, wherein the Venturi vacuum enables control of fluid flow resistance and/or fluid flow velocity.

General Definitions

Terms and phrases used in this document, and variations thereof, unless otherwise expressly stated, should be construed as open ended as opposed to limiting. As examples of the foregoing: the term "including" should be read as mean "including, without limitation" or the like; the term "example" is used to provide exemplary instances of the item in discussion, not an exhaustive or limiting list thereof; and adjectives such as "conventional," "traditional," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although item, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount, or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the subject matter of the present invention. For example, the term "about," when referring to a value can be meant to encompass variations of, in some embodiments±100%, in some embodiments±50%, in some embodiments±20%, in some embodiments±10%, in some embodiments±5%, in some embodiments±1%, in some embodiments ±0.5%, and in some embodiments±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. Although the foregoing subject matter has been described in some detail by way of illustration and example for purposes of clarity of understanding, it will be understood by those skilled in the art that certain changes and modifications can be practiced within the scope of the appended claims.

The invention claimed is:

1. A microfluidic system based on active control of flow resistance in microfluidic channels, comprising:
   a) a microfluidic device comprising a housing, wherein the housing comprises a top end and a bottom end;
   b) a plurality of reagent chambers and a plurality of pressure-generating chambers, wherein the reagent chambers and the pressure-generating chambers are positioned in the housing, and wherein:
      i) the pressure-generating chambers produce a pressure-generating fluid using no mechanical moving parts;
      ii) the reagent chambers are connected by at least one gas channel at the top end of the housing to at least one of the pressure-generating chambers; and
      iii) the reagent chambers are connected by one or more liquid channels at the bottom end of the housing to one or more of the pressure-generating chambers;
   c) a top substrate enclosing the pressure-generating fluid chambers, wherein the top substrate comprises fluidic channels connecting the pressure-generating chambers to one or more vent holes, thereby enabling movement of one or more reagent fluids in the one or more liquid channels at the bottom end of the housing; and
   d) a bottom substrate enclosing the reagent chambers;

wherein the movement of the one or more reagent fluids is enabled by activating the one or more pressure-generating chambers to pump the pressure-generating fluid toward the one or more reagent chambers and controlling and balancing pressure of the pressure-generating fluid to achieve active flow resistance resulting in the movement of the one or more reagent fluids in a desired direction; and wherein the microfluidic system is configured to achieve passive flow resistance during filling of the microfluidic device with the pressure-generating fluid to prevent mixing of the pressure-generating fluid with the reagents when the microfluidic system is not in operation.

2. The microfluidic system of claim 1, wherein achieving passive flow resistance during filling of the microfluidic device comprises the steps of:
aa) filling the plurality of pressure-generating chambers with pressure-generating fluid;
bb) enclosing the housing and the plurality of pressure-generating fluid chambers, the gas channels, and the plurality of reagent chambers with the top substrate such that the fluidic channels make desired connections between the chambers and vent holes enabling movement of one or more reagent fluids in liquid channels at the bottom end of the housing; and
cc) inverting the microfluidic device and filling the plurality of reagent chambers with the one or more reagent fluids and enclosing the reagent chambers, the one or more reagent fluids, and the liquid channels with a bottom substrate at the bottom end of the housing.

3. The microfluidic system of claim 1, further comprising an automated electronics interface and software control configured to control and balance the pressure of the pressure-generating fluid, wherein the automated electronics interface and software control is programmed to execute a reproducible protocol for operation of the microfluidic device.

4. The microfluidic system of claim 1, wherein the pressure of the pressure-generating fluid in the plurality of pressure-generating chambers is generated using electrolytic gas evolution.

5. The microfluidic system claim 1, wherein the pressure of the pressure-generating fluid in the plurality of pressure-generating chambers is generated using thermal heating, catalytic heating, ultrasonic means, electrophoretic means, or dielectrophoretic means.

6. The microfluidic system of claim 1, wherein the microfluidic device is configured to control the pressure of the pressure-generating fluid electronically using electrodes, electronic contacts, and/or switches embedded in the housing.

7. The microfluidic system of claim 1, wherein the one or more reagent fluids comprise one or more reagents for extraction, amplification, or detection of one or more analytes comprising one or more biomarkers, nutrients, and/or chemicals.

8. The microfluidic system of claim 1, wherein the one or more pressure-generating fluids comprise aqueous or non-aqueous liquids.

9. The microfluidic system of claim 1, wherein the one or more vent-holes are embedded within the top substrate of the housing atop one or more pressure-generating chambers or one or more reagent chambers.

10. The microfluidic system of claim 1, wherein the pressure of the pressure-generating fluid ranges from about 0.1 psi to about 1,000 psi.

11. The microfluidic system of claim 1, wherein the pressure of the pressure-generating fluid ranges from about 0.1 psi to about 100 psi.

12. The microfluidic system of claim 1, wherein electrolytic gas evolution generates the pressure of the pressure-generating fluid by electrolysis of the pressure-generating fluid, wherein the pressure-generating fluid comprises water, an inorganic salt solution, or a conductive organic solution, and wherein electrolysis of the pressure-generating fluid produces a gas comprising oxygen, hydrogen, and/or chlorine.

13. The microfluidic system of claim 1, further comprising one or more electrodes for electrolytic gas evolution, wherein the one or more electrodes comprise anodic corrosion-stable noble metal electrodes or one or more anodically sacrificial electrodes, wherein the one or more anodically sacrificial electrodes comprise stainless steel, aluminum, copper, carbon, carbon inks, plated electrodes, and/or screen-printed electrodes.

14. The microfluidic system of claim 1, configured to enable the gas produced by electrolysis to control pH and/or conductivity reactions in the one or more of the plurality of reagent chambers.

15. The microfluidic system of claim 1, further comprising one or more gas permeable membranes atop the plurality of pressure generation chambers, wherein the one or more gas permeable membranes separate liquid and gas pressure-generating fluids in the pressure-generating chambers while allowing permeation of pressure-generating fluid into the fluidic channels without mixing between the pressure-generating fluid and the one or more reagent fluids in the plurality of reagent chambers.

16. The microfluidic system of claim 1, configured to pump the pressure-generating fluid toward one of the plurality of reagent chambers that comprises one of the vent holes, or wherein the pressure-generating fluid is pumped toward one of the plurality of pressure generation chambers that comprises a vent hole, thereby causing a high flow velocity and generating a Venturi vacuum, wherein the Venturi vacuum enables control of fluid flow resistance and/or fluid flow velocity.

17. A method for actively controlling flow resistance in microfluidic channels of a microfluidic system, comprising:
a) providing a microfluidic system comprising a microfluidic device, wherein the microfluidic device comprises:
i) a housing, wherein the housing comprises a top end and a bottom end;
ii) a plurality of reagent chambers and a plurality of pressure-generating chambers, wherein the reagent chambers and the pressure-generating chambers are positioned in the housing, and wherein:
aa) the pressure-generating chambers produce a pressure-generating fluid using no mechanical moving parts;
bb) the reagent chambers are connected by at least one gas channel at the top end of the housing to at least one of the pressure-generating chambers; and
cc) the reagent chambers are connected by one or more liquid channels at the bottom end of the housing to one or more of the pressure-generating chambers;
iii) a top substrate enclosing the pressure-generating fluid chambers, wherein the top substrate comprises fluidic channels connecting the pressure-generating chambers to one or more vent holes, thereby enabling movement of one or more reagent fluids in the one or more liquid channels at the bottom end of the housing; and iv) a bottom substrate enclosing the reagent chambers; wherein the microfluidic system is configured to achieve passive flow resistance during filling of the microfluidic device with the pressure-generating fluid to prevent mixing of the pressure-generating fluid with the reagents when the microfluidic system is not in operation; and b) activating the one or more pressure-generating chambers to pump the pressure-generating fluid toward the one or more reagent chambers and controlling and balancing pressure of the pressure-generating fluid to achieve active flow resistance resulting in the movement of the one or more reagent fluids in a desired direction, wherein the movement of the one or more reagent fluids is enabled.

18. The method of claim 17, comprising achieving passive flow resistance during filling of the microfluidic device, further comprising the steps of:

ai) filling the plurality of pressure-generating chambers with pressure-generating fluid;

bi) enclosing the housing and the plurality of pressure-generating fluid chambers, the gas channels, and the plurality of reagent chambers with the top substrate such that the fluidic channels make desired connections between the chambers and vent holes enabling movement of one or more reagent fluids in liquid channels at the bottom end of the housing; and ci) inverting the microfluidic device and filling the plurality of reagent chambers with the one or more reagent fluids and enclosing the reagent chambers, the one or more reagent fluids, and the liquid channels with a bottom substrate at the bottom end of the housing.

19. The method of claim 17, wherein the method is executed by an automated electronics interface and software control configured to control and balance the pressure of the pressure-generating fluid, wherein the automated electronics interface and software control is programmed to execute a reproducible protocol for operation of the microfluidic device.

20. The method of claim 17, wherein the pressure of the pressure-generating fluid in the plurality of pressure-generating chambers is generated using electrolytic gas evolution.

21. The method of claim 17, wherein the pressure of the pressure-generating fluid in the plurality of pressure-generating chambers is generated using thermal heating, catalytic heating, ultrasonic means, electrophoretic means, or dielectrophoretic means.

22. The method of claim 17, wherein the microfluidic device is configured to control the pressure of the pressure-generating fluid electronically using electrodes, electronic contacts, and/or switches embedded in the housing.

23. The method of claim 17, wherein the one or more reagent fluids comprise one or more reagents for extraction, amplification, or detection of one or more analytes comprising one or more biomarkers, nutrients, and/or chemicals.

24. The method of claim 17, wherein the one or more pressure-generating fluids comprise aqueous or non-aqueous liquids.

25. The method of claim 17, wherein the one or more vent-holes are embedded within the top substrate of the housing atop one or more pressure-generating chambers or one or more reagent chambers.

26. The method of claim 17, wherein the pressure of the pressure-generating fluid ranges from about 0.1 psi to about 1,000 psi.

27. The method of claim 17, wherein the pressure of the pressure-generating fluid ranges from about 0.1 psi to about 100 psi.

28. The method of claim 17, wherein electrolytic gas evolution generates the pressure of the pressure-generating fluid by electrolysis of the pressure-generating fluid, wherein the pressure-generating fluid comprises water, an inorganic salt solution, or a conductive organic solution, and wherein electrolysis of the pressure-generating fluid produces a gas comprising oxygen, hydrogen, and/or chlorine.

29. The method of claim 17, further comprising one or more electrodes for electrolytic gas evolution, wherein the one or more electrodes comprise anodic corrosion-stable noble metal electrodes or one or more anodically sacrificial electrodes, wherein the one or more anodically sacrificial electrodes comprise stainless steel, aluminum, copper, carbon, carbon inks, plated electrodes, and/or screen-printed electrodes.

30. The method of claim 17, wherein the microfluidic system is configured to enable the gas produced by electrolysis to control pH and/or conductivity reactions in the one or more of the plurality of reagent chambers.

31. The method of claim 17, wherein the microfluidic system further comprises one or more gas permeable membranes atop the plurality of pressure generation chambers, wherein the one or more gas permeable membranes separate liquid and gas pressure-generating fluids in the pressure-generating chambers while allowing permeation of pressure-generating fluid into the fluidic channels without mixing between the pressure-generating fluid and the one or more reagent fluids in the plurality of reagent chambers.

32. The method of claim 17, wherein the microfluidic system is configured to pump the pressure-generating fluid toward one of the plurality of reagent chambers that comprises one of the vent holes, or wherein the pressure-generating fluid is pumped toward one of the plurality of pressure generation chambers that comprises a vent hole, thereby causing a high flow velocity and generating a Venturi vacuum, wherein the Venturi vacuum enables control of fluid flow resistance and/or fluid flow velocity.

* * * * *